(12) United States Patent
Gudmundsson et al.

(10) Patent No.: US 7,244,740 B2
(45) Date of Patent: Jul. 17, 2007

(54) IMIDAZO-PYRIDINE DERIVATIVES FOR USE IN THE TREATMENT OF HERPES VIRAL INFECTION

(75) Inventors: Kristjan Gudmundsson, Durham, NC (US); Brian A Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 226 days.

(21) Appl. No.: 10/489,056

(22) PCT Filed: Sep. 23, 2002

(86) PCT No.: PCT/US02/30056

§ 371 (c)(1),
(2), (4) Date: Mar. 9, 2004

(87) PCT Pub. No.: WO03/031446

PCT Pub. Date: Apr. 17, 2003

(65) Prior Publication Data

US 2004/0248917 A1 Dec. 9, 2004

Related U.S. Application Data

(60) Provisional application No. 60/327,705, filed on Oct. 5, 2001.

(51) Int. Cl.
C07D 471/04 (2006.01)
A61K 31/4188 (2006.01)

(52) U.S. Cl. ...................................... 514/275; 544/331

(58) Field of Classification Search ................ 544/331; 514/275
See application file for complete search history.

(56) References Cited

U.S. PATENT DOCUMENTS

| | | | |
|---|---|---|---|
| 4,576,952 A | 3/1986 | Hurst et al. |
| 4,621,089 A | 11/1986 | Ward et al. |
| 4,670,432 A | 6/1987 | Ward et al. |
| 4,719,218 A | 1/1988 | Bender et al. |
| 4,794,114 A | 12/1988 | Bender et al. |
| 4,985,444 A | 1/1991 | Shiokawa et al. |
| 5,145,858 A | 9/1992 | Adams et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |
| 6,207,675 B1 | 3/2001 | Carry et al. |

2004/0176396 A1 9/2004 Biftu et al.

FOREIGN PATENT DOCUMENTS

| | | |
|---|---|---|
| EP | 0 404 190 A1 | 6/1990 |
| EP | 0 404 190 B1 | 6/1990 |
| EP | 0403251 | 6/1990 |
| EP | 0 379 979 | 8/1990 |
| EP | 0404190 | 12/1990 |
| EP | 0 467 248 B1 | 7/1991 |
| EP | 0 497 258 A2 | 1/1992 |
| FR | 2 757 059 | 6/1998 |
| JP | 2001006877 | 6/1999 |
| WO | EP 0 364 204 A1 | 10/1989 |
| WO | WO 91 00092 | 1/1991 |
| WO | WO 91 19497 | 12/1991 |
| WO | WO 92/10190 | 6/1992 |
| WO | WO 92/10498 | 6/1992 |
| WO | WO 92/10499 | 6/1992 |
| WO | WO 95 00501 | 1/1995 |
| WO | WO 96 06840 | 3/1996 |
| WO | WO 96/16040 | 5/1996 |
| WO | WO 96 21667 | 7/1996 |
| WO | WO 96 31509 | 10/1996 |
| WO | WO 96/34866 | 11/1996 |
| WO | WO 96 41625 | 12/1996 |
| WO | WO 96 41626 | 12/1996 |

(Continued)

OTHER PUBLICATIONS

Bosseray et al., PubMed Abstract (Pathol Biol (Paris) 50(8):483-92) Oct. 2002.*

(Continued)

*Primary Examiner*—Deepak Rao
(74) *Attorney, Agent, or Firm*—Valerie L. Phillips

(57) ABSTRACT

The present invention provides compounds of formula (I):

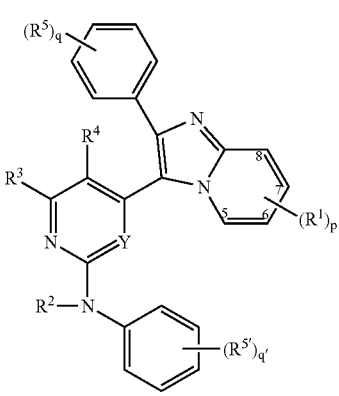

wherein all variables are as defined herein, pharmaceutical compositions containing the same, processes for preparing the same and their use as pharmaceutical agents.

21 Claims, No Drawings

FOREIGN PATENT DOCUMENTS

| | | |
|---|---|---|
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 00615 | 1/2001 |
| WO | WO 01 14375 | 3/2001 |
| WO | WO 01/96335 | 12/2001 |
| WO | WO 02/16359 | 2/2002 |
| WO | WO 02/18382 | 3/2002 |
| WO | WO 02 18382 | 3/2002 |
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Razonable et al., PubMed Abstract (Herpes 10(3):60-5) Dec. 2003.*

Vane, J. et al. "Towards a Better Aspirin." Nature, vol. 367, Jan. 20, 1994, pp. 215-216.

Carter, J. et al. "Recently Reported Inhibitors of Cyclooxygenase-2." Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitor Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

* cited by examiner

IMIDAZO-PYRIDINE DERIVATIVES FOR USE IN THE TREATMENT OF HERPES VIRAL INFECTION

CROSS REFERENCES TO RELATED APPLICATIONS

This application is a 371 Application of PCT/US02/30056, filed 23 Sep. 2002, which claims Priority to U.S. Application Ser. No. 60/327,705, filed 5 Oct. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV-1 and HSV-2), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the U.S. alone, 40 million individuals are infected with HSV-2, a number that is expected to increase to 60 million by 2007. Over 80% of individuals infected with HSV-2 are unaware they carry and spread the virus, and of those diagnosed less than 200% received oral therapies. The net result is that less than 50% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella Zoster Virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

PCT Publication No. WO 91/00092 to SmithKline Beecham Corp. refers to imidazo[1,2-a]pyridine compounds of formula (I)

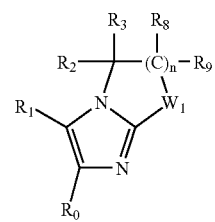

wherein:

$W_1$ is —$(CR_4R_5)$—$(CR_6R_7)$—, —$CR_5$=$CR_7$—, —N=$CR_7$—, —$S(O)_m$— or —O—; one of $R_1$ and $R_0$ is 4-pyridyl or $C_{1-4}$alkyl-4-pyridyl, provided that when $R_1$ is $C_{1-4}$alkyl-4-pyridyl the alkyl substituent is located at the 2-position of the pyridine ring, and the other of $R_1$ and $R_0$ is (a) phenyl or monosubstituted phenyl wherein said substituent is $C_{1-3}$alkylthio, $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2-alkenyl-1-sulfinyl, 1-acyloxy-1-alkylthio, $C_{1-2}$alkoxy, halo, $C_{1-4}$alkyl or Z wherein Z is —S—S—$Z_1$ and $Z_1$ is phenyl or $C_{1-9}$alkyl; or (b) disubstituted phenyl wherein said substituents are independently $C_{1-3}$alkylthio, $C_{1-2}$alkoxy, halo or $C_{1-4}$alkyl; or (c) disubstituted phenyl wherein one of said substituents is $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2alkenyl-1-sulfinyl, or 1-acyloxy-1-alkylthio and the other is $C_{1-2}$alkoxy, halo or $C_{1-4}$alkyl; or (d) disubstituted phenyl wherein the substituents are the same and are $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2alkenyl-1-sulfinyl, or 1-acyloxy-1-alkylthio or wherein the substituents together form a methylene dioxy group; or (e) monosubstituted phenyl wherein said substituent is

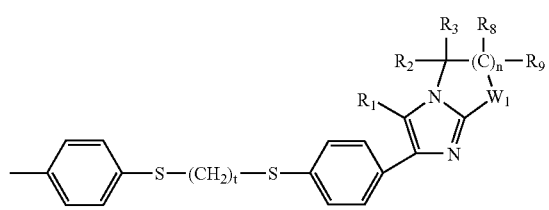

t is 0 or 1; $W_1$, $R_1$, $R_2$, $R_3$, $R_4$, $R_5$, $R_6$, $R_7$, $R_8$ and $R_9$ are as defined herein;

provided that:

1) when $W_1$ is —$(CR_4R_5)$—$(CR_6R_7)$— then
   n is 0 or 1;
   and $R_2$, $R_3$, $R_4$, $R_5$, $R_6$, $R_7$, $R_8$ and $R_9$ are independently —H or $C_{1-2}$alkyl; and
   when $R_1$ or $R_0$ is 4-pyridyl, the other of $R_1$ and $R_0$ is other than mono-$C_{1-2}$alkoxy-substituted phenyl or mono-halo-substiuted phenyl; or
   when n is O, $R_4$ and $R_5$ together are oxo; $R_4$ and $R_5$ are both fluoro, or one of $R_4$ and $R_5$ is H and the other is OH;

2) when $W_1$ is —$CR_5$=$CR_7$— or —N=$CR_7$— then
   n is 1;
   $R_3$, $R_5$, $R_7$ and $R_9$ are independently —H or $C_{1-2}$alkyl; and
   $R_2$ and $R_8$ together represent a double bond in the B ring such that the B ring is an aromatic pyridine or pyrimidine ring;

3) when $W_1$ is —$S(O)_m$— then
   m is 0, 1 or 2;
   n is 1 or 2;
   $R_3$ and $R_9$ are independently —H or $C_{1-2}$alkyl;
   $R_2$ and $R_8$ are independently —H or $C_{1-2}$alkyl or $R_2$ and $R^8$ together represent a double bond in the B ring such that the B ring is an aromatic thiazole ring;

further provided that:

(a) when $R_2$ and $R_8$ are independently —H or $C_{1-2}$alkyl and $R_1$ or $R_0$ is 4-pyridyl, then the other of $R_1$ and $R_0$ is other than mono-$C_{1-2}$alkoxy-substituted phenyl or mono-halo-substituted phenyl; and (b) when $R_2$ and $R_8$ together represent a double bond in the B ring such that the B ring is an aromatic thiazole ring, the m is 0 and n is 1; and 4) when $W_1$ is —O— then
   n is 1;
   $R_3$ and $R_9$ are independently —H or $C_{1-2}$alkyl; and
   $R_2$ and $R_8$ together represent a double bond in the B ring such that the
   B ring is an aromatic oxazole ring;

or a pharmaceutically acceptable salt thereof for use in the inhibition of interleukin-1 and tumor necrosis factor production by monocytes and/or macrophages.

PCT Publication No. WO 01/14375 to AstraZeneca AB relates to imidazo[1,2-a]pyridine and pyrazolo[2,3-a]pyridine derivatives of formula (I)

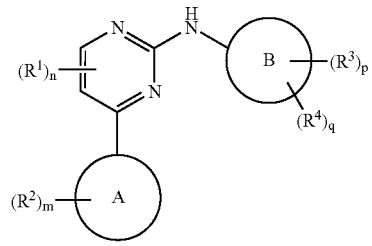

wherein Ring A is a imidazo[1,2-a]pyridine or pyrazolo[2,3-a]pyrid-3-yl; $R^2$ is as defined therein, m is 0–5; wherein the values of $R^2$ may be the same or different; $R^1$ is as defined therein; n is 0 to 2, wherein the values of $R^1$ may be the same or different; Ring B is phenyl or phenyl fused to a $C_{5-7}$cycloalkyl ring; $R^3$ is as defined therein; p is 0–4; wherein the values of $R^3$ may be the same or different; $R^4$ is as defined therein; q is 0–2; wherein the values of $R^4$ may be the same or different; and whrein p+q≦5; or a pharmaceutically acceptable salt or an in vivo hydrolysable ester thereof. The use of the compounds of formula (I) in the inhibition of cell cycle kinases CDK2, CDK4 and CDK6 are also described.

PCT Publication No. Wo 96/34866 to Fujisawa Pharmaceutical Co. Ltd. relates to imidazo[1,2-a]pyridine and imidazo[1,2-a]pyridezine derivatives of formula (I)

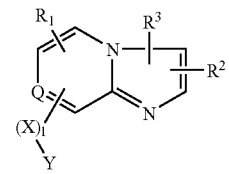

wherein X is vinylene or a group of formula (a):
—NHCO—, —$NHSO_2$—, —OCO—, $OCH_2$—, —NHCOCO—, —NHCOCH=CH—,
—$NHCOCH_2$—, —NHCONH or —$N(R^5)$—CO—, Y is heterocyclic group which may have one or more suitable substituent(s), or aryl which may have one or more suitable substituent(s), Q is CH or N, and I is an integer of 0 or 1, which are the inhibitors of bone resorption and bone metabolism, to processes for preparation thereof, to a pharmaceutical compositon comprising the same and to a method for the treatment of disease caused by abnormal bone metabolism in human being or an animal.

U.S. Pat. No. 5,498,774 and European Patent No. 0 404 190 to Mitsudera et al., relates to condensed heterocyclic compounds of the general formula (I):

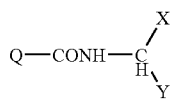

wherein Q is a condensed heterocyclic group having a nitrogen atom in the bridgehead which is unsubstituted or substituted, X is a hydrogen atom or a group attached through C, O, S or N, and Y is an electron attractive group; or its salt which is useful as an agricultural chemical.

BRIEF SUMMARY OF THE INVENTION

According to a first aspect of the invention there is provided a compound of formula (I):

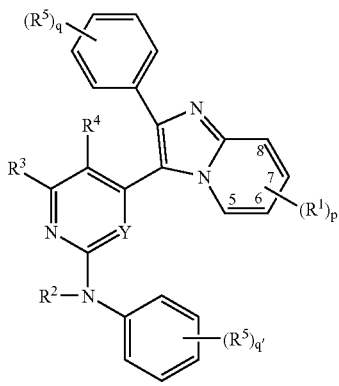

wherein:
p is 0, 1 or 2;
each $R^1$ is the same or different and is independently selected from the group consisting of halo, alkyl, alkenyl, alkynyl, cycloalkyl, cycloalkenyl, Ay, Het, —$OR^7$, —OHet, —$C(O)R^9$, —C(O)Het, —$CO_2R^9$, —$C(O)NR^7R^8$, —$C(NH)NR^7R^8$, —$S(O)_nR^9$, —$S(O)_2NR^7R^8$, —$NR^7R^8$, —$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or
two adjacent $R^1$ groups together with the atoms to which they are bonded form a $C_{5-6}$ cycloalkyl or 5- or 6-membered heterocyclic group containing 1 or 2 heteroatoms;
each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R^{11}$, —$C(NH)NR^9R^{11}$, —$SO_2R^{10}$, —$SO_2NR^9R^{11}$, —$R^{10}$cycloalkyl, —$R^{10}OR^9$ and —$R^{10}NR^9R^{11}$;
each $R^9$ and $R^{11}$ are the same or different and are independently selected from the group consisting of H, alkyl, cycloalkyl, —$R^{10}$cycloalkyl, —$R^{10}OH$, —$R_{10}(OR^{10})_w$ where w is 1–10, and —$R^{10}NR^{10}R^{10}$;
each $R^{10}$ is the same or different and is independently selected from the group consisting of alkyl, cycloalkyl, alkenyl, cycloalkenyl and alkynyl;
Ay is aryl;
Het is a 5- or 6-membered heterocyclic or heteroaryl group;
$R^2$ is selected from the group consisting of H, alkyl and cycloalkyl;
n is 0, 1 or 2;
Y is N or CH;
$R^3$ and $R^4$ are the same or different and are each independently selected from the group consisting of H, halo, alkyl, alkenyl, cycloalkyl, Ay, Het, —$OR^7$, —$C(O)R^7$, —$CO_2R^7$, —$SO_2NHR^9$, —$NR^7R^8$, —NHHet and —$NHR^{10}$Het;
q and q' are the same or different and are each independently selected from the group consisting of 0, 1, 2 and 3; and
each $R^5$ and $R^{5'}$ are the same or different and are independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —C(O)Ay, —C(O)Het, —$CO_2R^9$, —$C(O)NR^7R^8$, —$C(O)NR^7$Ay, —C(O)N H $R^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^1$Het, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR_{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ or $R^5$ groups together with the atoms to which they are bonded form a $C_{5-6}$ cycloalkyl or aryl;

or a pharmaceutically acceptable salt, solvate or physiologically functional derivative thereof.

In another aspect of the invention there is provided a pharmaceutical composition comprising a compound of formula (I), or a pharmaceutically acceptable salt, solvate or physiologically functional derivative thereof. In one embodiment, the pharmaceutical compostion may further comprise a pharmaceutically acceptable carrier or diluent. In one embodiment, the pharmaceutical composition further comprises an antiviral agent selected from the group consisting of aciclovir and valaciclovir.

In a third aspect of the invention, there is provided a method for the prophylaxis or treatment of a herpes viral infection in an animal, particularly a human. The method comprises administering to the animal a therapeutically effective amount of a compound of formula (I), or a pharmaceutically acceptable salt, solvate or physiologically functional derivative thereof. The herpes viral infection can be any of herpes simplex virus 1, herpes simplex virus 2, cytomegalovirus, Epstein Barr virus, varicella zoster virus, human herpes virus 6, human herpes virus 7, and human herpes virus 8.

In a fourth aspect, there is provided a method for the prophylaxis or treatment of a condition or disease associated with a herpes viral infection in an animal, particularly a human. The method comprises administering to the animal a therapeutically effective amount of the compound of formula (I), or a pharmaceutically acceptable salt, solvate or physiologically functional derivative thereof.

In another aspect, there is provided a process for preparing a compound of formula (I), wherein Y is N; and $R^3$ and $R^4$ are both H. The process comprises reacting a compound of formula (VI):

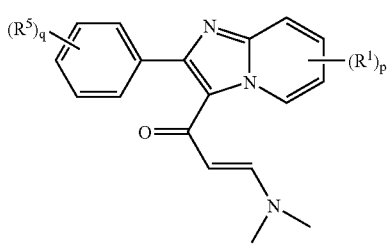

VI wherein p, $R^1$, q, and $R^5$ are as defined above in connection with compounds of formula (I);

with a compound of formula (VII):

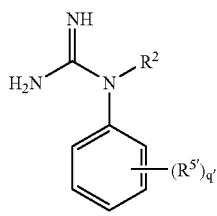

VII wherein $R^2$, q' and $R^{5'}$ are as defined above in connection with compounds of formula (I).

In another aspect, the present invention provides a process for preparing a compound of formula (I) wherein Y is N; $R^3$ is selected from the group consisting of H, alkyl, alkenyl, cycloalkyl, Ay, Het, —C(O)$R^7$, —CO$_2R^7$, —SO$_2$NHR$^9$ and —NR$^7R^8$ (where $R^7$ and $R^8$ are not H); and $R^4$ is H. The process comprises reacting a compound of formula (XI):

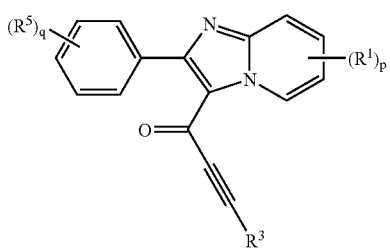

XI wherein p, $R^1$, q and $R^5$ are as defined above in connection with compounds of formula (I);

with a compound of formula (VII):

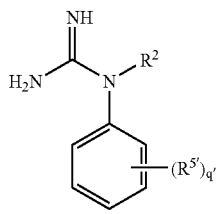

VII wherein $R^2$, q' and $R^{5'}$ are as defined above in connection with compounds of formula (I).

In another aspect, the present invention provides another process for preparing a compound of formula (I), wherein Y is N. The process comprises reacting a compound of formula (XIV):

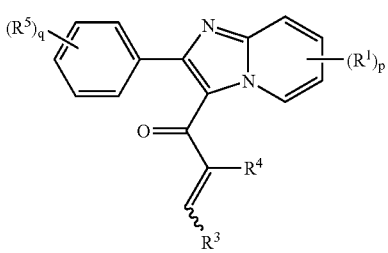

XIV wherein p, $R^1$, $R^3$, $R^4$, q and $R^5$ are as defined above in connection with compounds of formula (I);

with a compound of formula (vii)

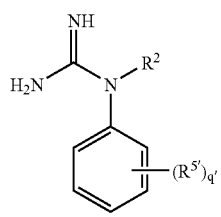

VII wherein $R^2$, q' and $R^{5'}$ are as defined above in connection with compounds of formula (I), followed by oxidation to prepare the compound of formula (I).

In another aspect, the present invention provides another process for preparing a compound of formula (I). The process comprises reacting a compound of formula (XV):

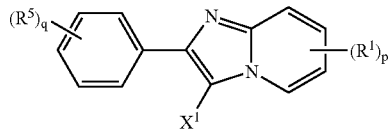

XV wherein p, $R^1$, q and $R^5$ are as defined above in connection with compounds of formula (I) and $X^1$ is halo;

with a compound of formula (XVI):

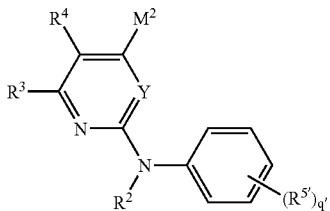

XVI wherein Y, $R^2$, $R^3$, $R^4$, q' and $R^{5'}$ are as defined above in connection with compounds of formula (I) and $M^2$ is selected from the group consisting of —B(OH)$_2$, —B(ORa)$_2$, —B(Ra)$_2$, —Sn(Ra)$_3$, Zn-halide, ZnRa, and Mg-halide where Ra is alkyl or cycloalkyl and halide is halo.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

The present invention provides a compound of formula (I), or a pharmaceutically acceptable salt, solvate or physiologically functional derivative thereof for use in therapy.

In yet another aspect, the present invention provides a compound of formula (I), or a pharmaceutically acceptable salt, solvate or physiologically functional derivative thereof for use in the prophylaxis or treatment of a herpes viral infection in an animal, particularly a human.

In yet another aspect, the present invention provides a compound of formula (I), or a pharmaceutically acceptable salt, solvate or physiologically functional derivative thereof for use in the prophylaxis or treatment of a condition or disease associated with a herpes viral infection in an animal, particularly a human.

In yet another aspect, the present invention provides the use of a compound of formula (I), or a pharmaceutically acceptable salt, solvate or physiologically functional derivative thereof for the preparation of a medicament for the prophylaxis or treatment of a herpes viral infection in an animal, particularly a human.

In yet another aspect, the present invention provides the use of a compound of formula (I), or a pharmaceutically acceptable salt, solvate or physiologically functional derivative thereof for the preparation of a medicament for the treatment or prophylaxis of a condition or disease associated with a herpes viral infection in an animal, particularly a human.

The present invention also provides a pharmacetuical composition comprising a compound of formula (I) for use in the prophylaxis or treatment of a herpes viral infection in an animal, particularly a human.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as compounds of formula (VI), (XI), (XIV), and (XV), the phrase "a compound of formula (numbed)" means a compound having that formula and pharmaceutically acceptable salts, solvates and physiologically functional derivatives thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl groups may be optionally substituted with one or more substituents selected from the group consisting of mercapto, nitro, cyano, and halo. Perhaloalkyl, such as trifluoromethyl is one particular alkyl group.

As used herein, the term "cycloalkyl" refers to a non-aromatic carbocyclic ring having from 3 to 8 carbon atoms and no carbon—carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted on any available carbon(s) with one or more substituents selected from the group consisting of mercapto, nitro, cyano, halo and alkyl.

As used herein, the term "alkenyl" refers to straight or branched hydrocarbon chains containing from 2 to 8 carbon atoms and at least one and up to three carbon—carbon double bonds. Examples of "alkenyl" as used herein include, but are not limited to ethenyl and propenyl. "Alkenyl" also includes substituted alkenyl. The alkenyl groups may optionally be substituted on any available carbon(s) with one or more substituents selected from the group consisting of mercapto, nitro, cyano, halo and alkyl.

As used herein, the term "cycloalkenyl" refers to a non-aromatic carbocyclic ring having from 3 to 8 carbon atoms (unless otherwise specified) and up to 3 carbon—carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon(s) with one or more substituents selected from the group consisting of mercapto, nitro, cyano, halo and alkyl.

As used herein, the term "alkynyl" refers to straight or branched hydrocarbon chains containing from 2 to 8 carbon atoms and at least one and up to three carbon—carbon triple bonds. Examples of "alkynyl" as used herein include, but are not limited to ethynyl and propynyl. "Alkynyl" also includes substituted alkynyl. The alkynyl groups may optionally be substituted on any available carbon(s) with one or more substituents selected from the group consisting of mercapto, nitro, cyano, halo and alkyl.

The term "halo" or "halogen" refers to the elements fluorine, chlorine, bromine and iodine.

The term "Ay" refers to monocyclic carbocyclic groups and fused bicyclic carbocyclic groups having from 5 to 12 carbon atoms (unless otherwise specified) and having at least one aromatic ring. Examples of particular aryl groups include but are not limited to phenyl, and naphthyl. "Aryl" also includes substituted aryl. Aryl may optionally be substituted on any available carbon with one or more substituents selected from the group consisting of halo, alkyl (including perhaloalkyl), alkenyl, cycloalkyl, cycloalkenyl, alkoxy, cycloalkoxy, amino, hydroxy, alkylhydroxy, alkylamine, cycloalkylamine, carboxy, carboxamide, sulfonamide, heterocyclic, heteroaryl, amidine, cyano, nitro and azido. Preferred aryl groups according to the invention include but are not limited to substituted and unsubstituted phenyl.

The term "heterocyclic" (or "heterocycle") refers to monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heterocyclic groups according to the invention include but are not limited to substituted and unsubstituted pyrrolidine, piperidine, morpholine, thiomorpholine and piperazine, and substituted variants thereof.

The term "heteroaryl" refers to aromatic monocyclic groups and aromatic fused bicyclic groups having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heteroaryl groups according to the invention include but are not limited to substituted and unsubstituted pyridine, furan, thiophene, pyrrole, imidazole, pyrazole, and pyrimidine, and substituted variants thereof.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

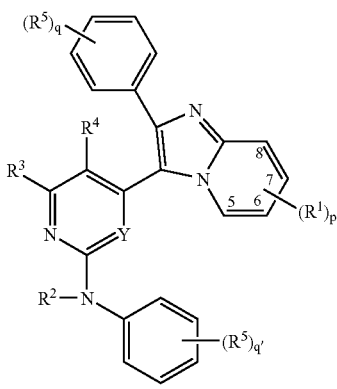

I wherein:
p is 0, 1 or 2;
each $R^1$ is the same or different and is independently selected from the group consisting of halo, alkyl, alkenyl, alkynyl, cycloalkyl, cycloalkenyl, Ay, Het, —$OR^7$, —OHet, —C(O)$R^9$, —C(O)Het, —$CO_2R^9$, —C(O)$NR^7R^8$, —C(NH)$NR^7R^8$, —S(O)$_nR_9$, —S(O)$_2NR^7R^8$—$NR^7R^8$,
—$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or
two adjacent $R^1$ groups together with the atoms to which they are bonded form a $C_{5-6}$ cycloalkyl or 5- or 6-membered heterocyclic group containing 1 or 2 heteroatoms;
each $R^7$ and $R^8$ are the same or different and are independently selected from the group consisting of H, alkyl, alkenyl, cycloalkyl, cycloalkenyl, —C(O)$R^9$, —$CO_2R^9$, —C(O)$NR^9R^{11}$, —C(NH)$NR^9R^{11}$, —$SO_2R^{10}$, —$SO_2NR^9R^{11}$, —$R^{10}$cycloalkyl, —$R^{10}OR^9$ and —$R^{10}NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R_{10}$($OR^{10}$)$_w$ where w is 1–10, and —$R^{10}NR^{10}R^{10}$;
each $R^{10}$ is the same or different and is independently selected from the group consisting of alkyl, cycloalkyl, alkenyl, cycloalkenyl and alkynyl;
Ay is aryl;
Het is a 5- or 6-membered heterocyclic or heteroaryl group;
$R^2$ is selected from the group consisting of H, alkyl and cycloalkyl;
n is 0, 1 or 2;
Y is N or CH;
$R^3$ and $R^4$ are the same or different and are each independently selected from the group consisting of H, halo, alkyl, alkenyl, cycloalkyl, Ay, Het, —$OR^7$, —C(O)$R^7$, —$CO_2R^7$, —$SO_2NHR^9$, —$NR^7R^8$, —NHHet and —$NHR^{10}$Het;
q and q' are the same or different and are each independently selected from the group consisting of 0, 1, 2 and 3; and
each $R^5$ and $R^{5'}$ are the same or different and are independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Het, —C(S)$NR^9R^{11}$, —C(NH)$NR^7R^8$, —C(NH)$NR^7$Ay, —S(O)$_nR^9$, —S(O)$_2NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}$C(O)$R^9$, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}$NHC(NH)$NR^9R^{11}$, cyano, nitro and azido; or two adjacent $R_5$ or $R^{5'}$ groups together with the atoms to which they are bonded form a $C_{5-6}$ cycloalkyl or aryl;

and pharmaceutically acceptable salts, solvates and physiologically functional derivatives thereof.

In one class of compounds of formula (I), Y is CH. In another class of compounds of formula (I), Y is N.

In one particular class of compounds of formula (I), p is 1 or 2. In one embodiment, p is 1. In one embodiment, p is 2. In one embodiment, p is 2 and optionally two adjacent $R^1$ groups together with the atoms which they are bonded, form a $C_{5-6}$ cycloalkyl or 5- or 6-membered heterocyclic group. The phrase "two adjacent $R^1$ groups" refers to two $R^1$ groups, each bonded to adjacent carbon atoms on the imidazol-pyridine ring. In the embodiment where two adjacent $R^1$ groups together with the atoms to which they are bonded form a cycloalkyl or heterocyclic group, p is typically 2, 3 or 4; more typically 2.

$R^1$ may be in the 5, 6, 7 and/or 8 position. In one embodiment, p is 1 and $R^1$ is in the C-8 position. In one embodiment, p is 1 and $R^1$ is in the C-6 position. In one embodiment p is 2 and one $R^1$ is in the C-8 position and one $R^1$ is in the C-6 position.

One class of compounds of formula (I) includes those compounds defined wherein at least one $R^1$ group contains an aryl, heterocyclic or heteroaryl moiety (in one embodiment, at least one $R^1$ group contains a heterocyclic or heteroaryl moiety) and two adjacent $R^1$ groups together with the atoms to which they are bonded do not form a $C_{5-6}$ cycloalkyl or 5- or 6-membered heterocyclic group. Another class of compounds of formula (I) includes those compounds defined where no $R^1$ group contains an aryl, heterocyclic or heteroaryl moiety (in one embodiment no $R^1$ group contains a heterocyclic or heteroaryl moiety) and two adjacent $R^1$ groups together with the atoms to which they are bonded do not form $C_{5-6}$ cycloalkyl or a 5- or 6-membered heterocyclic group. Another class of compounds of formula (I) includes those compounds defined wherein p is 2, no $R^1$ group contains an aryl, heterocyclic or heteroaryl moiety (or in one embodiment no $R^1$ group contains a heterocyclic or heteroaryl moiety) and two adjacent $R^1$ groups together with the atoms to which they are bonded form a $C_{5-6}$ cycloalkyl or 5- or 6-membered heterocyclic group containing 1 or 2 heteroatoms.

In the embodiment where $R^1$ contains a heterocyclic or heteroaryl moiety, each $R^1$ is the same or different and is typically selected from the group consisting of Het, —OHet, —C(O)Het, —NHHet and —$R^{10}$Het, or any subset thereof. In the embodiment where $R^1$ contains an aryl, heterocyclic or heteroaryl moiety, each $R^1$ is the same or different and is typically selected from the group consisting of Ay, Het, —OHet, —C(O)Het, —$NR^7$Ay, —NHHet and —$R^{10}$Het, or any subset thereof. In the embodiment where no $R^1$ contains an aryl, heterocyclic or heteroaryl moiety, each $R^1$ is the same or different and is typically selected from the group consisting of halo, alkyl, alkenyl, alkynyl, cycloalkyl, cycloalkenyl, —$OR^7$, —$C(O)R^9$, —$CO_2R^9$ (or —$CO_2R^{10}$), —$C(O)NR^7R^8$, —$C(NH)NR^7R^8$, —$S(O)_nR^9$, —$S(O)_2NR^7R^8$, —$NR^7R^8$, —$R^{10}$cycloalkyl, —$R^{10}R^9$, —$R^{10}SO_2NHCOR^9$, —$R^{10}NR^7R^8$, cyano, nitro and azido, or any subset thereof. In the embodiment where no $R^1$ contains a heterocyclic or heteroaryl moiety but may contain an aryl moiety, each $R^1$ is the same or different and is typically selected from the group consisting of halo, alkyl, alkenyl, alkynyl, cycloalkyl, cycloalkenyl, Ay, —$OR^7$, —$C(O)R^9$, —$CO_2R^9$ (or —$CO_2R^{11}$), —$C(O)NR^7R^8$, —$C(NH)NR^7R^8$, —$S(O)_nR^9$, —$S(O)_2NR^7R^8$, —$NR^7R^8$, —$NR^7$Ay, —$R^{10}$cycloalkyl, —$R^{10}OR^9$, —$R^{10}SO_2NHCOR^9$, —$R^{10}NR^7R_8$, cyano, nitro and azido, or any subset thereof.

When two adjacent $R^1$ groups together with the atoms to which they are bonded form a $C_{5-6}$ cycloalkyl or 5- or 6-membered heterocyclic group having 1 or 2 heteroatoms, p is 2. By "two adjacent $R^1$ groups" is meant that two $R^1$ groups are bonded to adjacent carbon atoms. In such embodiments, each $R^1$ group may be the same or different and is typically selected from the group consisting of alkyl, —$OR^7$, —$NR^7R^8$ and —$S(O)_nR^9$. For example, in one embodiment two adjacent $R^1$ groups are —$OR^7$ and together with the atoms to which they are bonded, they form a heterocyclic group such as:

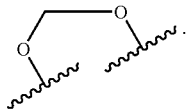

In another embodiment, two adjacent $R^1$ groups are alkyl and together with the atoms to which they are bonded, they form a cycloalkyl group such as:

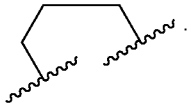

In another embodiment two adjacent $R^1$ groups are defined as —$OR^7$ and —$NR^7R^8$ respectively and together with the atoms to which they are bonded, they form a heterocyclic group such as:

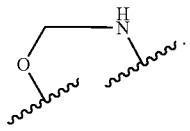

From these examples, additional embodiments can be readily ascertained by those skilled in the art.

In one embodiment, two $R^1$ groups together with the atoms to which they are bonded do not form a $C_{5-6}$ cycloalkyl or 5- or 6-membered heterocyclic group.

In one embodiment (particularly when Y is CH), each $R^1$ is the same or different and is independently selected from the group consisting of halo, alkyl, alkenyl, alkynyl, cycloalkyl, cycloalkenyl, Ay, Het, —$OR^7$, —OHet, —$C(O)R^9$, —C(O)Het, —$CO_2R_{10}$, —$C(NH)NR^7R^8$, —$S(O)_nR^9$, —$S(O)_2NR^7R^8$, —$NR^7R^8$, —$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or two adjacent $R^1$ groups together with the atoms to which they are bonded form a $C^{5-6}$ cycloalkyl or 5- or 6-membered heterocyclic group containing 1 or 2 heteroatoms.

In one embodiment, each $R^1$ is the same or different and is independently selected from the group consisting of halo, alkyl, cycloalkyl, Ay, Het, —$OR^7$, —$C(O)R_9$, —C(O)Het, —$CO_2R^9$, —$S(O)_nR^9$, —$S(O)_2NR^7R^8$, —$NR^7R^8$, —$NR^7$Ay, —NHHet, —$R^{10}$cycloalkyl, —$R^{10}$Het, —$R^{10}OR^9$, —$R^{10}NR^7R^8$, cyano, nitro and azido, or any subset thereof. More particularly, each $R^1$ is the same or different and is independently selected from the group consisting of halo, alkyl, Het, —$OR^7$, —C(O)Het, —$S(O)_n R^9$, —$S(O)_2NR^7R^8$, —$NR^7R^8$, —$NR^7$Ay and —NHHet, or any subset thereof. In one embodiment, each $R^1$ is the same or different and is independently selected form the group consisting of halo, alkyl, Het, —$OR^7$, —$S(O)_nR^9$, —$NR^7R_8$ and —NHHet, or any subset thereof. Particular compounds of formula (I) are defined wherein each $R^1$ is the same or different and is independently selected from the group consisting of halo, Het, —$NR^7R^8$ and NHHet, or any subset thereof. In another embodiment, $R^1$ is $NR^7R^8$; more particularly where $R^7$ and $R^8$ are selected from the group consisting of H, alkyl and cycloalkyl.

More specifically in one embodiment, each $R^1$ is the same or different and is independently selected from the group consisting of halo, —O-alkyl, —S-alkyl, —NH$_2$, —NHalkyl, —NHcycloalkyl, —N(alkyl)(alkyl), —N(alkyl)(cycloalkyl), Het, —Nalkyl-O-alkyl, and —NHAy, or any subset thereof. Specific examples of some particular $R^1$ groups are selected from the group consisting of Br, Cl, —O-butyl, —NH$_2$, —NH-methyl, —NH-butyl, —N(CH$_3$)$_2$, —NH-cyclopentyl, —NH-cyclopropyl, —NH-isopropyl, —NH-phenyl, —N(CH$_2$)$_2$OCH$_3$, pyrrolidine, and morpholine, or any subset thereof.

In one embodiment, $R^7$ and $R^8$ are each the same or different and are independently selected from the group consisting of H, alkyl, cycloalkyl, —C(O)R$^9$, —R$^{10}$-cycloalkyl, —R$^{10}$OR$^9$ and —R$^{10}$NR$^9$R$^{11}$, or any subset thereof. More particularly, $R^7$ and $R^8$ are each the same or different and are independently selected from the group consisting of H, alkyl, cycloalkyl, and —R$^{10}$-cycloalkyl, or any subset thereof. In one embodiment, $R^7$ and $R^8$ are each the same or different and are independently selected from the group consisting of H, alkyl and cycloalkyl, or any subset thereof.

The group —R$^{10}$(OR$^{10}$)$_w$ in the definition of $R^9$ and $R^{11}$ refers to a PEG-like chain. In one embodiment, $R^9$ and $R^{11}$ are each the same or different and are independently selected from the group consisting of H, alkyl, cycloalkyl, and —R$^{10}$-cycloalkyl, or any subset thereof. More particularly, $R^9$ and $R^{11}$ are each the same or different and are independently selected from the group consisting of H and alkyl.

In one embodiment $R^{10}$ is alkyl or cycloalkyl; more particularly alkyl.

In one embodiment, $R^2$ is H or alkyl, or any subset thereof. In one embodiment, $R^2$ is H.

In another embodiment, the compounds of formula (I) include those compounds defined where at least one of $R^3$ and $R^4$ contains an aryl, heterocyclic or heteroaryl moiety (or in one embodiment at least one of $R^3$ and $R^4$ contains a heterocyclic or heteroaryl moiety but exclude aryl moeities). Another embodiment includes those compounds of formula (I) where neither $R^3$ nor $R^4$ contain an aryl, heterocyclic or heteroaryl moiety (or more particularly, neither contain a heterocyclic or heteroaryl moiety but may contain an aryl moiety). Based on the guidance given above for $R^1$, one skilled in the art can readily determine the list of appropriate groups defining $R^3$ and $R^4$ which contain or exclude aryl, heterocyclic or heteroaryl moeities.

In one embodiment, $R^3$ is selected from the group consisting of H, halo, alkyl, Ay, —OR$^7$, —CO$_2$R$^7$ and —NR$^7$R$^8$, or any subset thereof. More particularly, $R^3$ is selected from the group consisting of H, halo, alkyl, —OR$^7$ and —NR$^7$R$^8$, or any subset thereof. In one particular embodiment $R^3$ is H or alkyl. In one embodiment $R^3$ is H.

In one embodiment, $R^4$ is selected from the group consisting of H, halo, alkyl, Ay, —OR$^7$, —CO$_2$R$^7$ and —NR$^7$R$^8$, or any subset thereof. More particularly, $R^4$ is selected from the group consisting of H, halo, alkyl, —OR$^7$, and —NR$^7$R$^8$, or any subset thereof. In one particular embodiment $R^4$ is H or alkyl. In one embodiment $R^4$ is H.

In one embodiment q is 0, 1 or 2. In one embodiment, q is 0. In one particular embodiment, q is 1.

$R^5$ may be in the ortho, meta or para position.

Another class of compounds of formula (I) includes those compounds defined wherein at least one $R^5$ group contains an aryl, heterocyclic or heteroaryl moiety (in one embodiment, a heterocyclic or heteroaryl moiety) and two adjacent $R^5$ groups together with the atoms to which they are bonded do not form a $C_{5-6}$ cycloalkyl or aryl. Another class of compounds of formula (I) includes those compounds defined wherein q is 3 at least one $R^5$ group contains an aryl, heterocyclic or heteroaryl moiety (in one embodiment, a heterocyclic or heteroaryl moiety) and two adjacent $R^5$ groups together with the atoms to which they are bonded form a $C_{5-6}$ cycloalkyl or aryl. Another class of compounds of formula (I) includes those compounds defined where no $R^5$ group contains an aryl, heterocyclic or heteroaryl moiety (or in one embodiment no $R_5$ group contains a heterocyclic or heteroaryl moeity) and two adjacent $R^5$ groups together with the atoms to which they are bonded do not form a $C_{5-6}$ cycloalkyl or aryl. Another class of compounds of formula (I) includes those compounds defined wherein q is 2 or 3, no $R_5$ group contains an aryl, heterocyclic or heteroaryl moiety (or in one embodiment no $R_5$ group contains a heterocyclic or heteroaryl moiety) and two adjacent $R_5$ groups together with the atoms to which they are bonded form a $C_{5-6}$ cycloalkyl or aryl.

When two adjacent $R_5$ groups together with the atoms to which they are bonded form a $C_{5-6}$ cycloalkyl or aryl, q is typically 2 or 3; more particularly 2. By "two adjacent $R^5$ groups" is meant that two $R^5$ groups are bonded to adjacent carbon atoms. In such embodiments, each $R_5$ group may be the same or different and is typically selected from the group consisting of alkyl and alkenyl. A specific example of a cycloalkyl group formed from two adjacent $R^5$ groups together with the atoms to which they are bonded is described above in connection with the description of $R^1$ groups forming similar groups. Based on this guidance, examples of aryl groups formed from two adjacent $R_5$ groups together with the atoms to which they are bonded can be readily determined by those skilled in the art. In one embodiment, two $R_5$ groups together with the atoms to which they are bonded do not form a $C_{5-6}$ cycloalkyl or aryl.

In one embodiment, each $R_5$ group is the same or different and is independently selected from the group consisting of halo, alkyl, Ay, Het, —OR$^7$, —OAy, —CO$_2$R$^9$, —C(O)NR$^7$R$^8$, —S(O)$_2$NR$^7$R$^8$, —NR$^7$R$^8$, —NR$^7$Ay, —NHR$^{10}$Ay, cyano, nitro and azido, or any subset thereof. More particularly, each $R_5$ group is the same or different and is independently selected from the group consisting of halo, alkyl, Het, —OR$^7$, —S(O)$_2$NR$^7$R$_5$, —NR$^7$R$^8$, cyano and nitro, or any subset thereof. In one embodiment, each $R^5$ group is the same or different and is independently selected from the group consisting of halo, alkyl, —OR$^7$, —NR$^7$R$_5$ and cyano, or any subset thereof.

More specific examples of compounds of formula (I) are defined wherein each $R^5$ is the same or different and is independently selected from the group consisting of halo (e.g., fluoro, chloro, bromo), alkyl (e.g., methyl and trifluoromethyl), O-alkyl (e.g., O-methyl, O-isobutyl, and

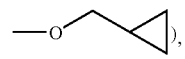

O-allyl, cyano and —NH—(CH$_2$-cyclopropyl), or any subset thereof.

In one embodiment q' is 0, 1 or 2. In one embodiment, q' is 0. In another embodiment, q' is 1.

$R^{5'}$ may be in the ortho, meta or para position.

Another class of compounds of formula (I) includes those compounds defined wherein at least one $R^{5'}$ group contains an aryl, heterocyclic or heteroaryl moiety (in one embodiment a heterocyclic or heteroaryl moiety) and two adjacent $R^{5'}$ groups together with the atoms to which they are bonded do not form a $C_{5-6}$ cycloalkyl or aryl. Another class of compounds of formula (I) includes those compounds defined wherein q is 3, at least one $R^{5'}$ group contains an aryl, heterocyclic or heteroaryl moiety (in one embodiment, a heterocyclic or heteroaryl moiety) and two adjacent $R^{5'}$ groups together with the atoms to which they are bonded form a $C_{5-6}$ cycloalkyl or aryl. Another class of compounds of formula (I) includes those compounds defined where no $R^{5'}$ group contains an aryl, heterocyclic or heteroaryl moiety (or in one embodiment no $R^{5'}$ group contains a heterocyclic or heteroaryl moiety) and two adjacent $R^{5'}$ groups together with the atoms to which they are bonded do not form a $C_{5-6}$ cycloalkyl or aryl. Another class of compounds of formula (I) includes those compounds defined wherein q is 2 or 3, no $R^{5'}$ group contains an aryl, heterocyclic or heteroaryl moiety (or in one embodiment no $R^5$ group contains a heterocyclic or heteroaryl moiety) and two adjacent $R^5$ groups together with the atoms to which they are bonded form a $C_{5-6}$ cycloalkyl or aryl.

When two adjacent $R^{5'}$ groups together with the atoms to which they are bonded form a $C_{5-6}$ cycloalkyl or aryl, q is typically 2 or 3; more typically 2. By "two adjacent $R^{5'}$ groups' is meant that two $R^{5'}$ groups are bonded to adjacent carbon atoms. In such embodiments, each $R_{5'}$ group may be the same or different and is typically selected from the group consisting of alkyl and alkenyl. A specific example of a cycloalkyl formed from two adjacent $R^{5'}$ groups together with the atoms to which they are bonded is described above in connection with the description of $R^1$ groups forming similar rings. Based on this guidance, aryl rings formed from two adjacent $R^{5'}$ groups together with the atoms to which they are bonded can be readily determined by those skilled in the art. In one embodiment, two $R_{5'}$ groups together with the atoms to which they are bonded do not form a $C_{5-6}$ cycloalkyl or aryl.

In one embodiment, each $R^{5'}$ group is the same or different and is independently selected from the group consisting of halo, alkyl, Ay, Het, —$OR^7$, —OAy, —C(O)Ay, —C(O)Het, —$CO_2R^9$, —$C(O)_2NR^7R^8$, —$S(O)_2NR_7R_8$, —$NR^7R^8$, cyano, nitro and azido, or any subset thereof. More particularly, each $R^{5'}$ group is the same or different and is independently selected from the group consisting of halo, alkyl, Het, —$OR^7$—C(O)Ay, —C(O)Het, —$C(O)NR^7R^8$, —$S(O)_2NR^7R^8$, —$NR^7R^8$, cyano and azido, or any subset thereof. In one embodiment, each $R^{5'}$ group is the same or different and is independently selected from the group consisting of halo, alkyl, —$OR^7$—C(O)Ay, —C(O)Het and —$NR^7R^8$, or any subset thereof.

More specific examples of compounds of formula (I) are defined wherein each $R^{5'}$ is the same or different and is independently selected from the group consisting of halo (e.g., fluoro, chloro, bromo), alkyl (e.g., methyl, trifluoromethyl), O-alkyl (e.g., O-methyl, O-isobutyl, and

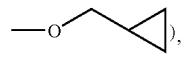

O-allyl, —NH—$CH_3$ and —$N(CH_3)_2$, or any subset thereof.

It is to be understood that the present invention includes all combinations and subsets of the particular and specific groups defined hereinabove.

Preferred compounds of formula (I) include but are not limited to:

4-[8-Chloro-2-(3-methoxyphenyl)imidazo[1,2-α]pyridin-3-yl]-N-phenylpyrimidin-2-amine;

N-Cyclopentyl-3-[2-(cyclopentylamino)-4-pyrimidinyl]-2-(3-methoxyphenyl)imidazo-[1,2-α]pyridin-8-amine;

4-[8-Chloro-2-(4-methylphenyl)imidazo[1,2-α]pyridin-3-yl]-N-phenylpyrimidin-2-amine;

3-(2-Anilino-4-pyrimidinyl)-N-cyclopentyl-2-(4-methylphenyl)imidazo[1,2-α]pyridin-8-amine; and 4-[8-Chloro-2-(3-nitrophenyl)imidazo[1,2-α]pyridin-3-yl]-N-(4-fluorophenyl)pyrimidin-2-amine;

and pharmaceutically acceptable salts, solvates and physiologically functional derivatives thereof.

It will be appreciated by those skilled in the art that the compounds of the present invention may also be utilized in the form of a pharmaceutically acceptable salt solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, partiucularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compound of formula (I) are conventional in the art. See, for example, Burger's Medicinal Chemistry And Drug Discovery, 5th Edition, Vol 1: Principles And Practice.

As will be apparent to those skilled in the art, in the processes descibed below for the preparation of compounds of formula (I), certain intermediates, including but not limited to compounds of formulas (VI, XI, XIV and XV), may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) and intermediates used in the processes of preparing compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV) (including CMV in organ transplant patients being treated with immunosuppressants), Epstein Barr virus (EBV), varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV; and multiple sclerosis which ahs been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty, viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B or hepatitis C viruses, human papilloma virus (HPV) and HIV.

The present invention thus provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with a herpes viral infection in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a a cardiovascular condition such as atherosclerosis, coronary artery disease or restenosis (particularly restenosis following surgery such as angioplasty), which comprises administering to the animal a therapeutically effective amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of a condition or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical composition. The pharmaceutical composition may comprise a pharmaceutically acceptable carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I) and optionally also one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations suitable for topical (e.g., dermal) or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, typically 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, fameyclovir, ganciclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir or valaciclovir; the use of such combination in the treatment of a viral infection and the preparation of a medicament for the treatment of a viral infection, and a method of treating a viral infection comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N; and $R^3$ and $R^4$ are both H, may be conveniently prepared by a general process outlined in Scheme 1 below.

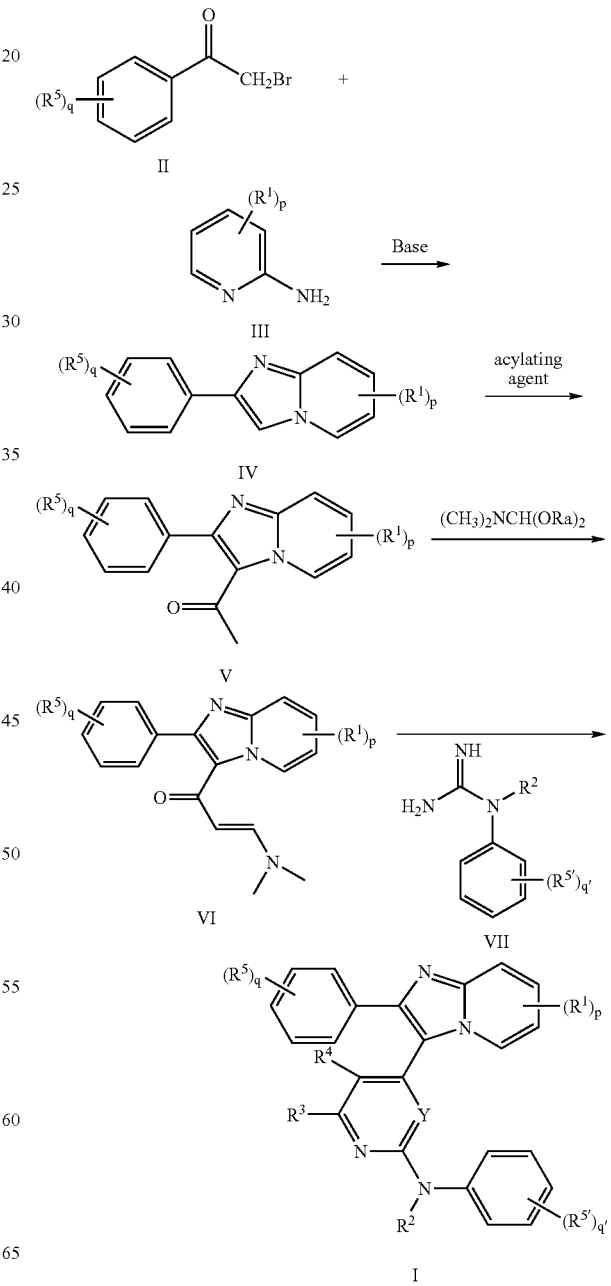

wherein:

p is 0, 1 or 2;

each $R^1$ is the same or different and is independently selected from the group consisting of halo, alkyl, alkenyl, alkynyl, cycloalkyl, cycloalkenyl, Ay, Het, —$OR^7$, —OHet, —C(O)$R^9$, —C(O)Het, —$CO_2R^9$, —C(O)$NR^7R_8$, —C(NH)$NR^7R_8$, —S(O)$_nR^9$, —S(O)$_2NR^7R^8$, —$NR^7R_8$, —$NR^7$Ay, —NHHet, —$R^{10}$cycloalkyl, —$R^{10}$Het, —$R^{10}OR^9$, —$R^{11}SO_2NHCOR^9$, —$R^{10}NR^7R^8$, cyano, nitro and azido; or two adjacent $R^1$ groups together with the atoms to which they are bonded form a $C_{5-6}$ cycloalkyl or 5- or 6-membered heterocyclic group containing 1 or 2 heteroatoms;

each $R^7$ and $R_8$ are the same or different and are independently selected from the group consisting of H, alkyl, alkenyl, cycloalkyl, cycloalkenyl, —C(O)$R^9$, —$CO_2R^9$, —C(O)$NR^9R^{11}$, —C(NH)$NR^9R^{11}$, —$SO_2R^{10}$, —$SO_2NR^9R^{11}$, —$R^{10}$cycloalkyl, —$R^{10}OR^9$ and —$R^{10}NR^9R^{11}$;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

$R^2$ is selected from the group consisting of H, alkyl and cycloalkyl;

n is 0, 1 or 2;

Y is N;

$R^3$ and $R^4$ are both H;

q and q' are the same or different and are each independently selected from the group consisting of 0, 1, 2 and 3;

each $R^5$ and $R^{5'}$ are the same or different and are independently selected from the group consisting of halo, alkyl, alkenyl, alkynyl, cycloalkyl, cycloalkenyl, Ay, Het, —$OR^7$—OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Het, —C(S)$NR^9R^{11}$, —C(NH)$NR^7R^8$, —C(NH)$NR^7$Ay, —S(O)$_nR^9$, —S(O)$_2NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ or $R_5$ groups together with the atoms to which they are bonded form a $C_{5-6}$ cycloalkyl or aryl; and Ra is alkyl or cycloalkyl.

Generally, the process for preparing the compounds of formula (I) wherein Y is N and $R^3$ and $R^4$ are both H, (all formulas and all other variables having been defined above in connection with Scheme 1) comprises the steps of:

(a) reacting an aminopyridine of formula (III) with a 2-bromoacetophenone of formula (II) to prepare a compound of formula (IV);

(b) acylating the compound of formula (IV) to prepare a compound of formula (V);

(c) reacting the compound of formula (V) with a dimethylformamide dialkyl acetal of formula $(CH_3)_2NCH(ORa)_2$ to prepare a compound of formula (VI); and (d) reacting the compound of formula (VI) with a compound of formula (VII) to prepare a compound of formula (I).

More specifically, compounds of formula (I) wherein Y is N and $R^3$ and $R^4$ are both H, can be prepared by reacting a compound of formula (VI) with a compound of formula (VII).

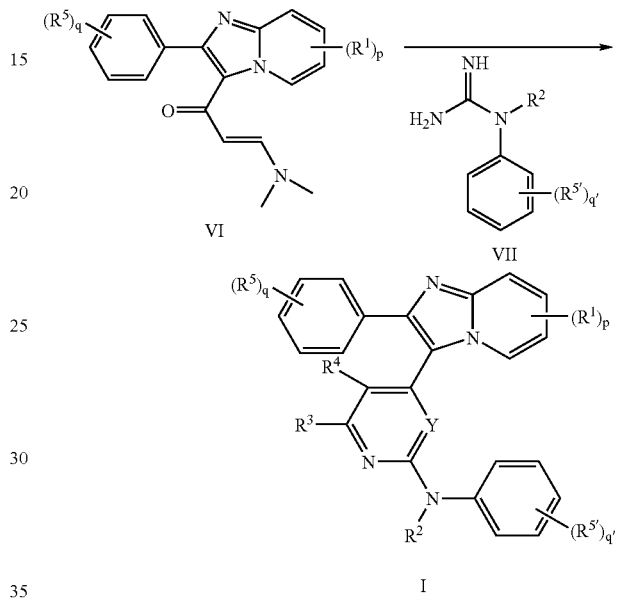

wherein all variables are as defined above in connection with Scheme 1.

This method can be readily carried out by mixing a compound of formula (VI) with a compound of formula (VII) in a suitable solvent, optionally in the presence of a base (preferably when the guanidine is in a salt form), and heating the reaction at 20–150° C. Typical solvents include lower alcohols such as methanol, ethanol, isopropanol, dimethylformamide, 1-methyl-2-pyrrolidinone and the like. The base is typically a sodium alkoxide, potassium carbonate, or an amine base such as triethylamine. In one embodiment, the solvent is 1-methyl-2-pyrrolidone and the base is potassium carbonate, or an amine base such as triethylamine.

The compounds of formula (VII) can be prepared according to conventional methods. One method for preparing the compounds of formula (VII) involves heating an appropriately substituted aniline with cyanamide in the presence of a protic acid in an alcohol solvent.

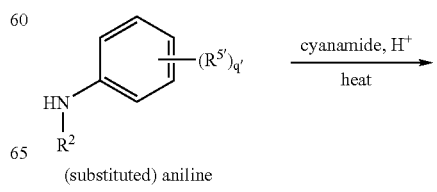

(substituted) aniline

-continued

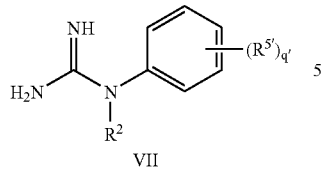

VII wherein all variables are as defined above in connection with Scheme 1.

This method is adapted from the procedures described in WO 00/78731 published 28 Dec. 2000, the subject matter of which is incorporated herein by reference in its entirety. Preferred acids include but are not limited to hydrochloric acid, nitric acid, and sulfuric acid. Suitable solvents will be readily apparent to those skilled in the art and include, for example, ethanol.

The substituted anilines are commercially available or may be prepared using conventional techniques.

Compounds of formula (VI) may be conveniently prepared by reacting a compound of formula (V) with a dimethylformamide dialkyl acetal of formula $(CH_3)_2NCH(ORa)_2$, wherein $R_a$ is alkyl or cycloalkyl.

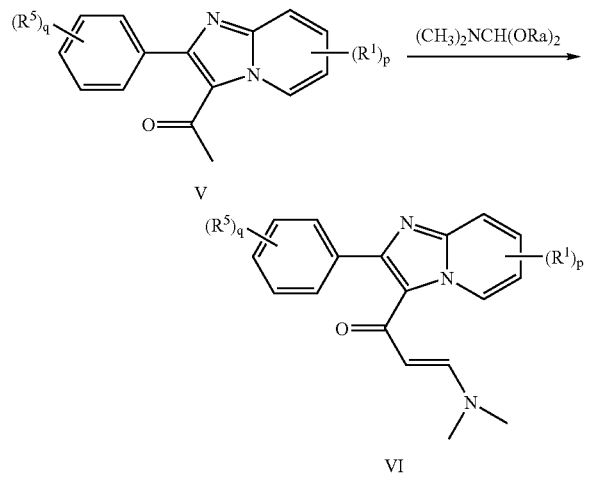

wherein all variables are as defined above in connection with Scheme 1.

Typical dimethylformamide dialkylacetal compounds for use in this method include but are not limited to dimethylformamide dimethylacetal and dimethylformamide di-tert-butylacetal.

The reaction is carried out by mixing a compound of formula M with the dimethylformamide dialkyl acetal, optionally with heating and optionally in the presence of solvent such as N,N-dimethylformamide.

Compounds of formula M may be conveniently prepared from compounds of formula (IV) using an acylation procedure.

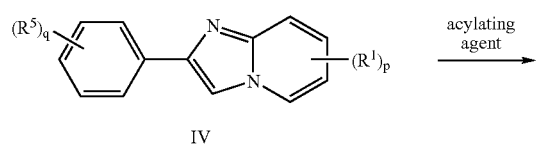

-continued

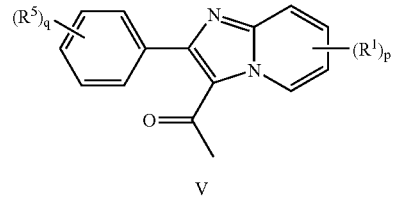

V wherein all variables are as defined above in connection with Scheme 1.

Typically the acylation is carried out by treating the compounds of formula (IV) with an acylating agent, optionally in the presence of an acid or Lewis acid catalyst optionally in an inert solvent with optional heating. Typical acylating agents will be readily determined by those skilled in the art. One acylating agent is acetic anhydride. Acid catalysts are also known to those skilled in the art. One acid catalyst for use in this reaction is sulfuric acid.

The reaction can also be carried out using N,N-dimethylacetamide and phosphorous oxychloride, optionally in an inert solvent with optional heating.

Compounds of formula (IV) are conveniently prepared by condensation of aminopyridines of formula (III) with 2-bromoacetophenones of formula (II) optionally in the presence of base.

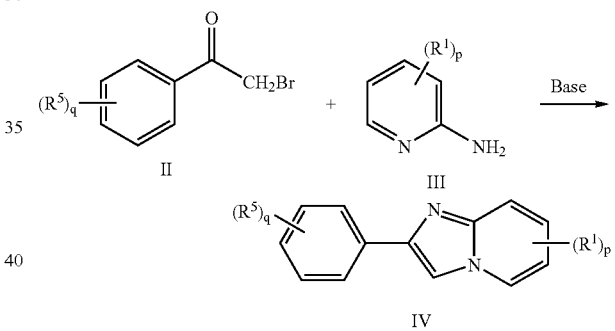

wherein all variables are as defined above in connection with Scheme 1.

The condensation of the aminopyridine of formula (III) with the 2-bromoacetophenone of formula (II) can be accomplished in a suitable solvent at a temperature of about 20–200° C., optionally in the presence of base. Suitable inert solvents include, but are not limited to, ethanol, isopropanol, N,N-dimethylformamide and the like. Suitable bases include sodium bicarbonate, sodium carbonate, potassium carbonate, sodium hydroxide and the like.

Compounds of formula (II) and (III) are commercially available or may be prepared using methods known to those skilled in the art.

In addition to the foregoing process for preparing certain compounds of formula (I), the present invention also provides certain intermediate compounds for use in the preparation of such compounds of formula (I) according to the foregoing process. Such intermediates are described in Scheme 1.

In a further embodiment of the present invention, compounds of formula (I) wherein Y is N; $R^3$ is selected from the group consisting of H, alkyl, alkenyl, cycloalkyl, Ay, Het, $-C(O)R^7$, $-CO_2R^7$, $-SO_2NHR^9$ and $-NR^7R^8$ (where $R^7$ and $R^8$ are not H); and $R^4$ is H, may be conveniently prepared by the process outlined in Scheme 2 below.

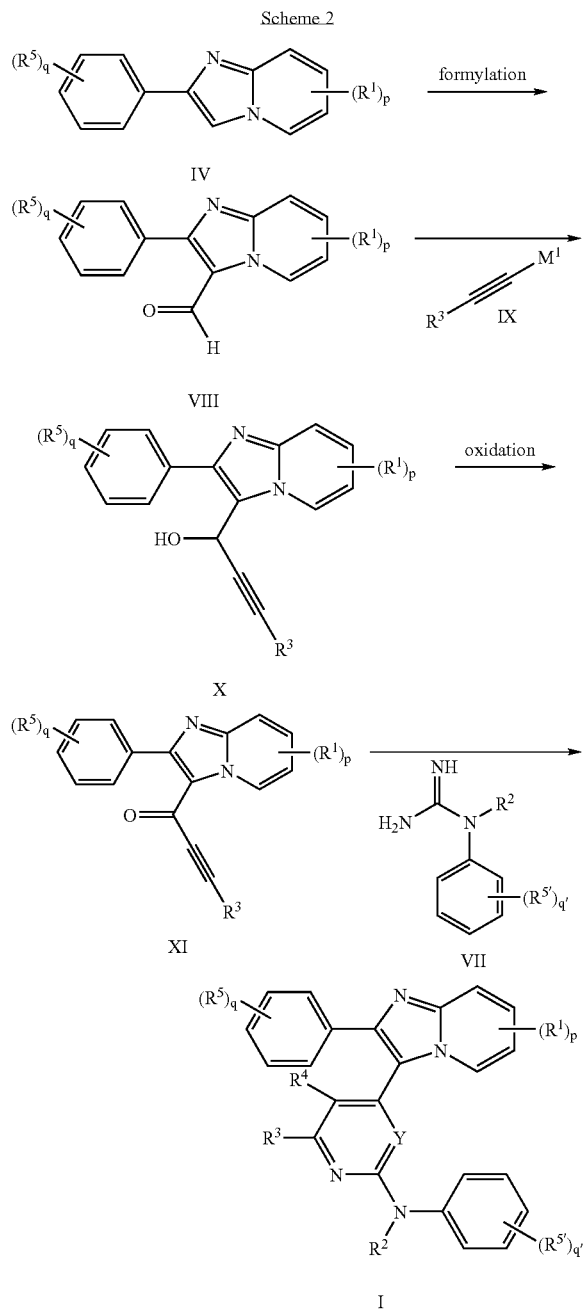

wherein:

p is 0, 1 or 2;

each $R^1$ is the same or different and is independently selected from the group consisting of halo, alkyl, alkenyl, alkynyl, cycloalkyl, cycloalkenyl, Ay, Het, —$OR^7$, —OHet, —$C(O)R^9$, —C(O)Het, —$CO_2R^9$, —$C(O)NR^7R^8$, —$C(NH)NR^7R^8$, —$S(O)_nR^9$, —$S(O)_2NR^7R_8$, —$NR^7R_8$, —$NR^7Ay$, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or two adjacent $R^1$ groups together with the atoms to which they are bonded form a $C_{5-6}$ cycloalkyl or 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R^{11}$, —$C(NH)NR^9R^{11}$, —$SO_2R_{10}$, —$SO_2NR^9R^{11}$, —$R^{10}$cycloalkyl, —$R^{10}OR^9$ and —$R^{10}NR^9R^{11}$;

each $R^9$ and $R^{11}$ are the same or different and are independently selected from the group consisting of H, alkyl, cycloalkyl, —$R^{10}$cycloalkyl, —$R^{10}OH$, —$R_{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

$R^2$ is selected from the group consisting of H, alkyl and cycloalkyl;

n is 0, 1 or 2;

Y is N;

$R^3$ is selected from the group consisting of H, alkyl, alkenyl, cycloalkyl, Ay, Het, —$C(O)R^7$, —$CO_2R^7$, —$SO_2NHR^9$ and —$NR^7R^8$ (where $R^7$ and $R_5$ are not H);

$R^4$ is H;

q and q' are the same or different and are each independently selected from the group consisting of 0, 1, 2 and 3;

each $R^5$ and $R^{5'}$ are the same or different and are independently selected from the group consisting of halo, alkyl, alkenyl, alkynyl, cycloalkyl, cycloalkenyl, Ay, Het, —$OR^7$, —OAy, —$OR^{10}Ay$, —OHet, —$OR^{10}$Het, —$C(O)R^9$, —C(O)Ay, —C(O)Het, —$CO_2R^9$, —$C(O)NR^7R^8$, —$C(O)NR_7Ay$, —$C(O)NHR^{10}Het$, —$C(S)NR^9R^{11}$, —$C(NH)NR^7R_8$, —$C(NH)NR^7Ay$, —$S(O)_nR^9$—$S(O)_2NR^7R_8$, —$S(O)_2NR^7Ay$, —$NR^7R^8$, —$NR^7Ay$, —NHHet, —$NHR^{10}Ay$, —$NHR^{10}Het$, —$R^{10}$cycloalkyl, —$R^{10}Het$, —$R^{10}OR^9$, —$R^{10}C(O)R^9$, —$R^{10}CO_2R^9$, —$R^{10}C(O)NR^9R^{11}$, —$R^{10}C(O)NR^7Ay$, —$R^{10}C(O)NHR^{10}Het$, —$R^{10}C(S)NR^9R^{11}$, —$R^{10}C(NH)NR^9R^{11}$, —$R^{11}SO_2R^9$, —$R^{10}SO_2NR^9R^{11}$, —$R^{10}SO_2NHCOR^9$, —$R^{10}NR^7R^8$, —$R^{10}NR^7Ay$, —$R^{10}NHC(NH)NR^9R^{11}$, cyano, nitro and azido; or two adjacent $R^5$ or $R^{5'}$ groups together with the atoms to which they are bonded form a $C_{5-6}$ cycloalkyl or aryl; and $M^1$ is Li, Mg-halide or cerium-halide, wherein halide is halo.

Generally, the process for preparing compounds of formula (I) wherein Y is N; $R^3$ is selected from the group consisting of H, alkyl, alkenyl, cycloalkyl, Ay, Het, —$C(O)R^7$, —$CO_2R^7$, —$SO_2NHR^9$ and —$NR^7R^8$ (where $R^7$ and $R^8$ are not H); and $R^4$ is H (all other variables having been defined above in connection with Scheme 2), comprises the following steps:

(a) formylating a compound of formula (IV) to prepare a compound of formula (VIII);

(b) reacting the compound of formula (VIII) with a compound of formula (IX) to prepare a compound of formula (X);

(c) oxidizing the compound of formula (X) to prepare a compound of formula (XI); and (d) reacting the compound of formula (XI) with a compound of formula (VII) to prepare a compound of formula (I).

More specifically, compounds of formula (I) wherein Y is N; $R^3$ is selected from the group consisting of H, alkyl, alkenyl, cycloalkyl, Ay, Het, —C(O)$R^7$, —CO$_2R^7$, —SO$_2$NH$R^9$ and —N$R^7R^8$ (where $R^7$ and $R^8$ are not H); and $R^4$ is H, may be prepared by reacting a compound of formula (XI) with a compound of formula (VII).

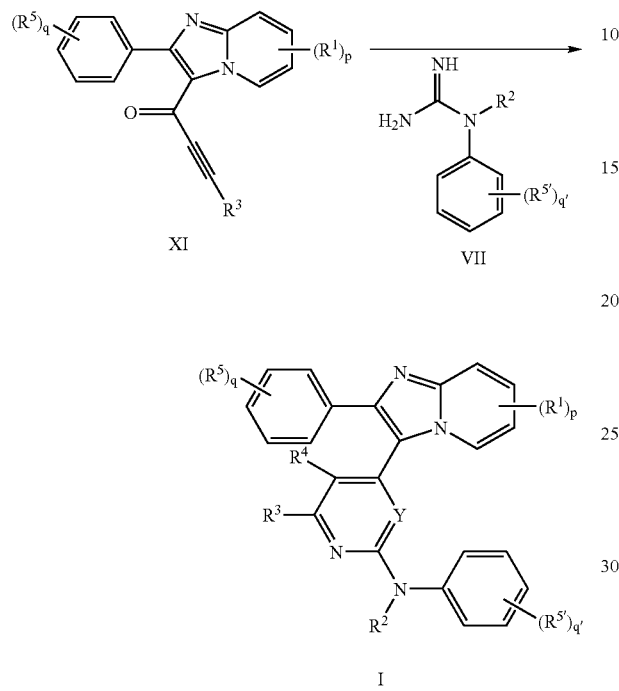

wherein all variables are as defined above in connection with Scheme 2.

This method can be readily carried out by mixing a compound of formula (XI) with a compound of formula (VII) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide, 1-methyl-2-pyrrolidinone and the like and the base is potassium carbonate, or an amine base such as triethylamine.

A compound of formula (XI) may be conveniently prepared by oxidation of a compound of formula (X).

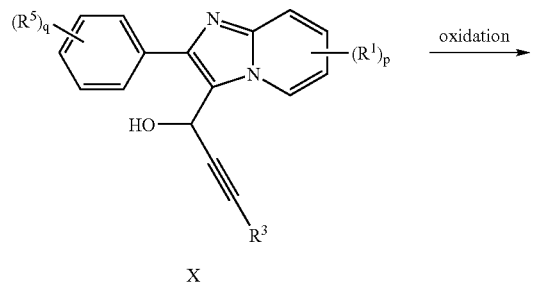

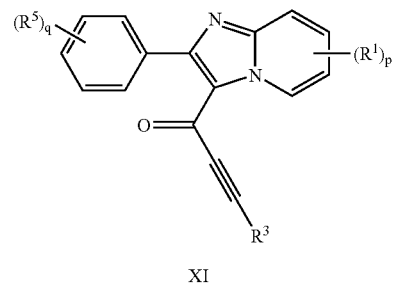

wherein all variables are as defined above in connection with Scheme 2.

Preferred oxidizing agents include but are not limited to, manganese dioxide, and the like, in an inert solvent. Suitable inert solvents include but are not limited to, dichloromethane, chloroform, N,N-dimethylformamide, ether, and the like. In another embodiment a compound of formula (X) is oxidized using oxidation methods well known to those skilled in the art of organic chemistry such as Swern oxidation (Omura, K.; Swern, D. *Tetrahedron,* 1978, 34, 1651) or Dess Martin periodinane oxidation (Dess, D. B.; Martin, J. C. *J. Org. Chem.,* 1983, 48, 4155).

A compound of formula (X) may be conveniently prepared by reacting a compound of formula (VIII) with a compound of formula (IX).

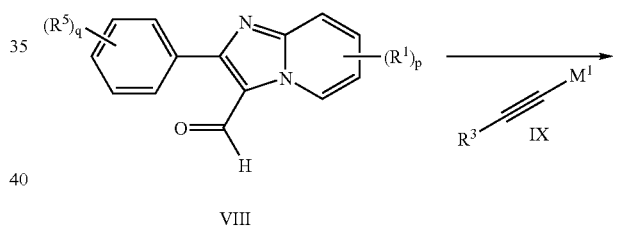

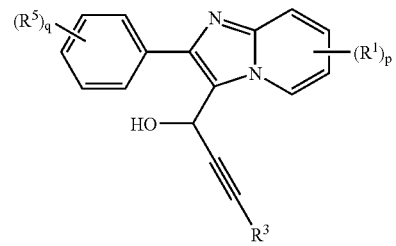

wherein all variables are as defined above in connection with Scheme 2.

Preferred metals ($M^1$) in the compounds of formula (IX) include but are not limited to, lithium, magnesium(II) halides, cerium(III) halides, and the like. A compound of formula (IX) may be purchased from commercial sources or prepared by methods known to one skilled in the art.

A compound of formula (VIII) may be conveniently prepared from a compound of formula (IV) by a formulation procedure.

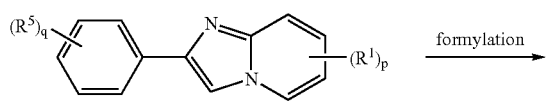

IV

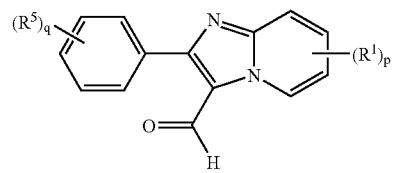

VIII wherein all variables are as defined above in connection with Scheme 2.

Typically the formulation is carried out via the Vilsmeier-Haack reaction. The Vilsmeier-Haack reagents can be purchased from commercial sources or prepared in situ. Preferable conditions include, but are not limited to treating compounds of formula (IV) with a premixed solution of phosphorous oxychloride in N,N-dimethylformamide optionally with heating the reaction to 50–150° C. The compounds of formula (IV) are prepared according to the process described in connection with Scheme 1 above.

In addition to the foregoing process for preparing certain compounds of formula (I), the present invention provides certain intermediate compounds for use in the preparation of such compounds of formula (I) according to the foregoing process. Such intermediates are described in Scheme 2 above.

Further, compounds of formula (I) wherein Y is N, may be conveniently prepared by a process outlined in Scheme 3 below.

Scheme 3

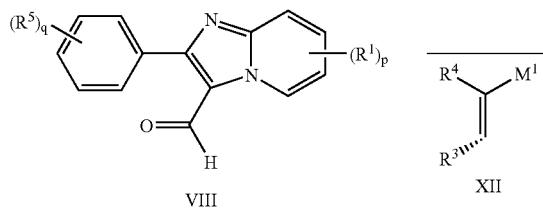

VIII

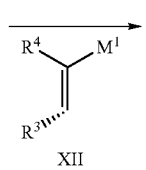

XII

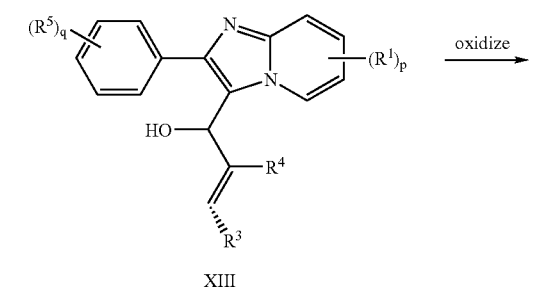

XIII

-continued

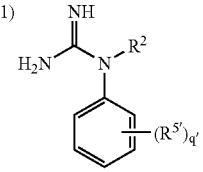

VII

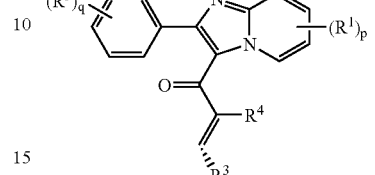

XIV

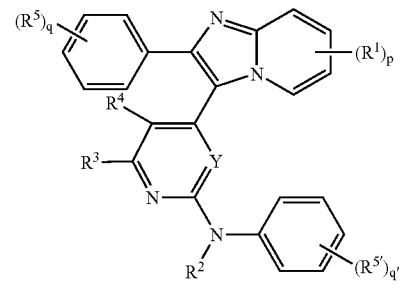

I wherein:

p is 0, 1 or 2;

each $R^1$ is the same or different and is independently selected from the group consisting of halo, alkyl, alkenyl, alkynyl, cycloalkyl, cycloalkenyl, Ay, Het, —$OR^7$, —OHet, —$C(O)R^9$, —C(O)Het, —$CO_2R^9$, —$C(O)NR^7R^8$, —$C(NH)NR^7R^8$, —$S(O)_nR^9$, —$S(O)_2NR^7R^8$, —$NR^7R^8$, —$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or two adjacent $R^1$ groups together with the atoms to which they are bonded form a $C_{5-6}$ cycloalkyl or 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R_{11}$, —$C(NH)NR^9R_{11}$, —$SO_2R^{10}$, —$SO_2NR^9R"$, —$R^{10}$cycloalkyl, —$R^{10}OR^9$ and —$R^{10}NR^9R^{11}$;

each $R^9$ and $R^{11}$ are the same or different and are independently selected from the group consisting of H, alkyl, cycloalkyl, —$R^{10}$cycloalkyl, —$R^{10}OH$, —$R_{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

R² is selected from the group consisting of H, alkyl and cycloalkyl;

n is 0, 1 or 2;

Y is N;

R³ and R⁴ are the same or different and are each independently selected from the group consisting of H, halo, alkyl, alkenyl, cycloalkyl, Ay, Het, —OR⁷, —C(O)R⁷, —CO₂R⁷, —SO₂NHR⁹, —NR⁷R⁸, —NHHet and —NHR¹⁰Het;

q and q' are the same or different and are each independently selected from the group consisting of 0, 1, 2 and 3;

each $R_5$ and $R_{5'}$ are the same or different and are independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, —C(O)R⁹, —C(O)Ay, —C(O) Het, —CO₂R⁹, —C(O)NR⁷R₈, —C(O)NR⁷Ay, —C(O)N HR¹⁰Het, —C(S)NR⁹R¹¹, —C(NH)NR⁷R₈, —C(NH)NR⁷Ay, —S(O)ₙR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰(O)R⁹, —R¹⁰CO₂R⁹, —R¹⁰(O)NR⁹R¹¹, —R¹⁰(O)NR⁷Ay, —R¹⁰C(O)N HR₁₀Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent $R_5$ or $R_5$ groups together with the atoms to which they are bonded form a $C_{5-6}$ cycloalkyl or aryl; and M¹ is Li, Mg-halide or cerium-halide, wherein halide is halo.

Generally, the process for preparing compounds of formula (I) wherein Y is N, (all formulas and all other variables having been defined above in connection with Scheme 3), comprises the following steps:

(a) reacting a compound of formula (VIII) with a compound of formula (XII) to prepare a compound of formula (XIII);

(b) oxidizing the compound of formula (XIII) to prepare a compound of formula (XIV); and (c) reacting the compound of formula (XIV) with a compound of formula (VII) followed by oxidation to prepare a compound of formula (I).

More specifically, compounds of formula (I) wherein Y is N, can be prepared by reacting a compound of formula (XIV) with a compound of formula (VII) followed by oxidative aromatization.

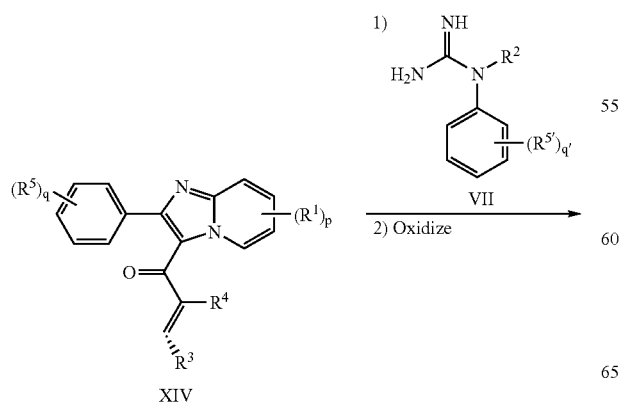

XIV

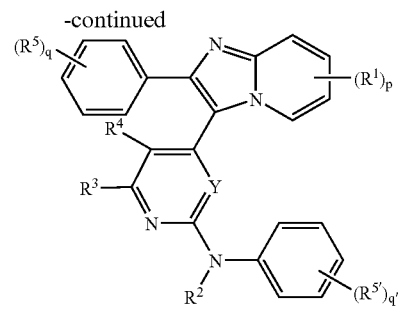

I wherein all variables are as defined above in connection with Scheme 3.

The condensation is conveniently carried out by treating the compound of formula (XIV) with a compound of formula (VII) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Preferably in the same reaction vessel, the dihydropyrimidine intermediate may be oxidized to a compound of formula (I) by the addition of an oxidizing agent. The reaction may be heated to 50–150° C. or performed at ambient temperature. Preferably, the oxidizing agent is oxygen (O₂), palladium on carbon, 2,3-dichloro-5,6-dicyano-1,4-benzoquinone, or the like.

A compound of formula (XIV) may be conveniently prepared by oxidation of a compound of formula (XIII).

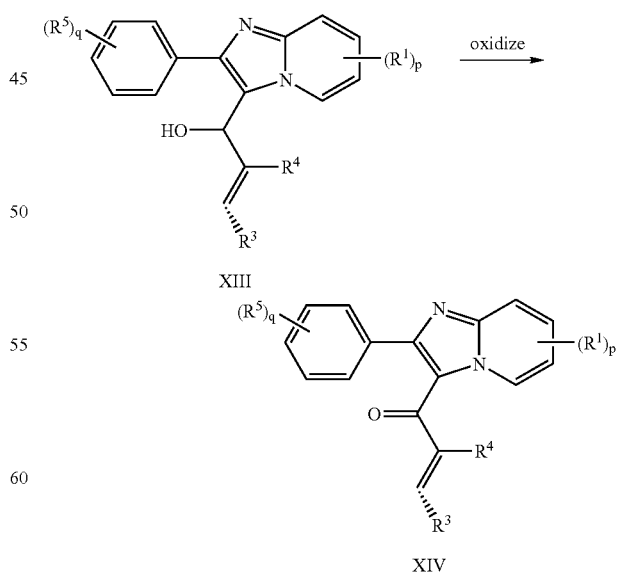

XIV wherein all variables are as defined above in connection with Scheme 3.

Preferred oxidizing agents for the oxidation of compounds of formula (XIII) include but are not limited to manganese dioxide, and the like. The oxidation is typically carried out in an inert solvent such as for example, dichloromethane, chloroform, N,N-dimethylformamide, ether, and the like. In another embodiment the compound of formula (XIII) is oxidized using oxidation methods well known to those skilled in the art of organic chemistry such as Swern oxidation (Omura, K.; Swern, D. *Tetrahedron,* 1978, 34, 1651) or Dess Martin periodinane oxidation (Dess, D. B.; Martin, J. C. *J. Org. Chem.,* 1983, 48, 4155).

A compound of formula (XIII) may be conveniently prepared by reacting a compound of formula (VIII) with a compound of formula (XII).

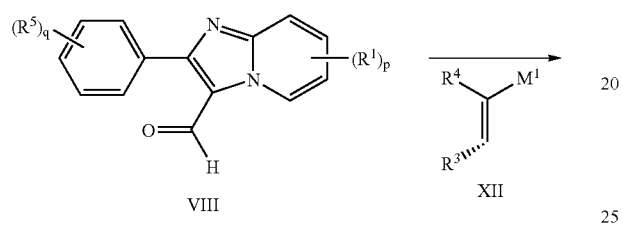

VIII    XII

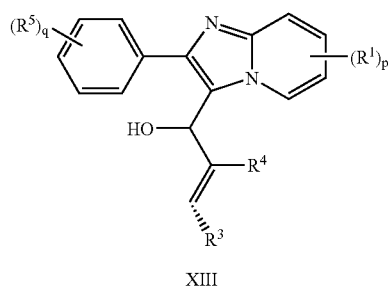

XIII wherein all variables are as defined above in connection with Scheme 3.

A compound of formula (XII) may be purchased from commercial sources or prepared by methods known to one skilled in the art.

The compounds of formula (VIII) may be prepared using the methods described in connection with Schemes 1 and 2 above.

In addition to the foregoing process for preparing certain compounds of formula (I), the present invention also provides certain intermediate compounds for use in the preparation of such compounds of formula (I) according to the foregoing process. Such intermediates are described above in Scheme 3.

A compound of formula (I), may be conveniently prepared by the process outlined in Scheme 4 below.

Scheme 4

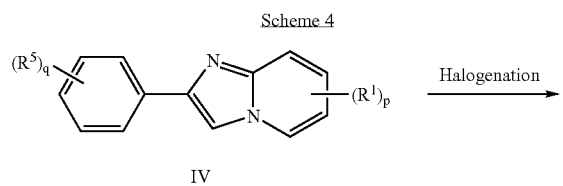

IV

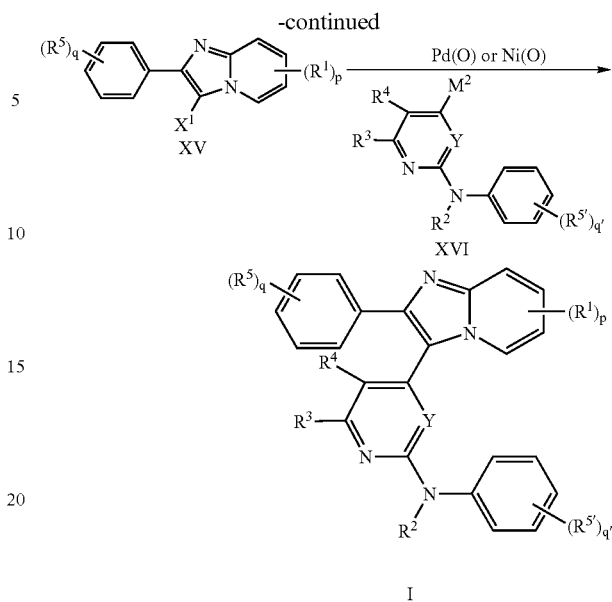

XV

XVI

I wherein:

$X^1$ is halo, particularly bromo or iodo;

p is 0, 1 or 2;

each $R^1$ is the same or different and is independently selected from the group consisting of halo, alkyl, alkenyl, alkynyl, cycloalkyl, cycloalkenyl, Ay, Het, —$OR^7$, —OHet, —$C(O)R^9$, —C(O)Het, —$CO_2R^9$, —$C(O)NR^7R^8$, —$C(NH)NR^7R^8$, —$S(O)_nR^9$, —$S(O)_2NR^7R^8$, —$NR^7R^8$, —$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or two adjacent $R^1$ groups together with the atoms to which they are bonded form a $C_{5-6}$ cycloalkyl or 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R^{11}$, —$C(NH)NR^9R^{11}$, —$SO_2R^{10}$, —$SO_2NR^9R^{11}$, —$R^{10}$cycloalkyl, —$R^{10}OR^9$ and —$R^{10}NR^9R^{11}$;

each $R^9$ and $R^{11}$ are the same or different and are independently selected from the group consisting of H, alkyl, cycloalkyl, —$R^{10}$cycloalkyl, —$R^{10}$OH, —$R_{10}$$(OR^{10})_w$ where w is 1–10, and —$R^{11}NR^1OR^{10}$;

each $R^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

$R^2$ is selected from the group consisting of H, alkyl and cycloalkyl;

n is 0, 1 or 2;

Y is N or CH;

$R^3$ and $R^4$ are the same or different and are each independently selected from the group consisting of H, halo, alkyl, alkenyl, cycloalkyl, Ay, Het, —$OR^7$, —$C(O)R^7$, —$CO_2R^7$, —$SO_2NHR^9$, —$NR^7R^8$, —NHHet and —$NHR^{10}$Het;

q and q' are the same or different and are each independently selected from the group consisting of 0, 1, 2 and 3;

each $R_5$ and $R_{5'}$ are the same or different and are independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O) $R^9$, —C(O)Ay, —C(O)Het, —$CO_2R^9$, —C(O)$NR^7R^8$, —C(O)$NR^7$Ay, —C(O)$NHR^{10}$Het, —C(S)$NR^9R^{11}$, —C(NH)$NR^7R^8$, —C(NH)$NR^7$Ay, —S(O)$_nR^9$, —S(O)$_2$$NR^7R_8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)R^9$, —$R^{11}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(N H)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ or $R^{5'}$ groups together with the atoms to which they are bonded form a $C_{5-6}$ cycloalkyl or aryl; and $M^2$ is —B(OH)$_2$, —B(ORa)$_2$, —B(Ra)$_2$, —Sn(Ra)$_3$, Zn-halide, ZnRa, or Mg-halide where Ra is alkyl or cycloalkyl and halide is halo.

Generally, the process for preparing a compound of formula (I) (all formulas and variables having been defined above in connection with Scheme 4), comprises the following steps:

(a) halogenating a compound of formula (IV) to prepare a compound of formula (XV); and (b) reacting the compound of formula (XV) with a compound of formula (XVI) to prepare a compound of formula (I).

More specifically, a compound of formula (I) wherein Y is N or CH can be prepared by reacting a compound of formula (XV) with a compound of formula (XVI).

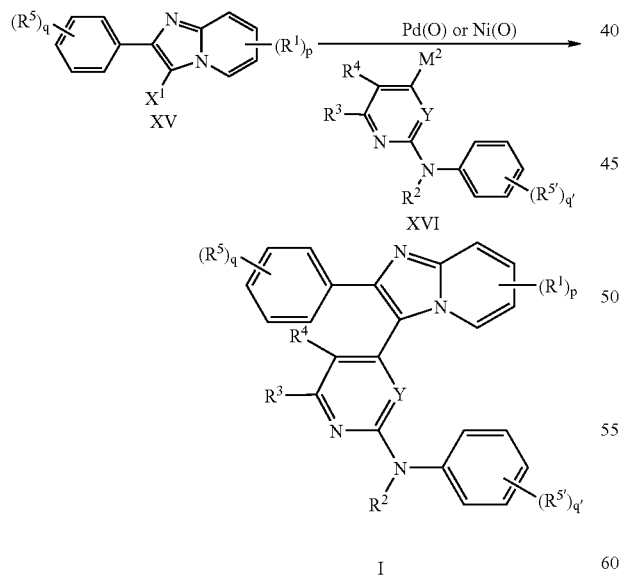

I wherein all variables are as defined above in connection with Scheme 4.

The reaction may be carried out in an inert solvent, in the presence of a palladium (O) or nickel (O) catalyst. The reaction may optionally be heated to about 50–150° C.

Preferably the reaction is performed by reacting equimolar amounts of a compound of formula (XV) with a Het-metal compound of formula (XVI), but the reaction may also be performed in the presence of an excess of the compound of formula (XVI). The palladium or nickel catalyst is typically present in 1–10 mol % compared to the compound of formula (XV). Examples of suitable palladium catalysts include but are not limited to, tetrakis(triphenylphosphine) palladium (O), dichlorobis(triphenyl-phosphine)palladium (II), tris(dibenzylideneacetone)dipalladium (O), and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XVI) is an arylboronic acid or ester or an arylborinate the reaction is more conveniently carried out by adding a base in a proportion equivalent to, or greater than, that of the compound of formula (XVI). Het-metal compounds of formula (XVI) may be obtained from commercial sources or prepared either as discreet isolated compounds or generated in situ using methods known to one skilled in the art (Suzuki, A. *J. Organomet Chem.* 1999, 576, 147; Stille, *J. Angew. Chem. Int Ed. Engl.* 1986, 25, 508; Snieckus, V. *J. Org. Chem.* 1995, 60, 292).

A compound of formula (XV) can be prepared from a compound of formula (IV) by a halogenation procedure.

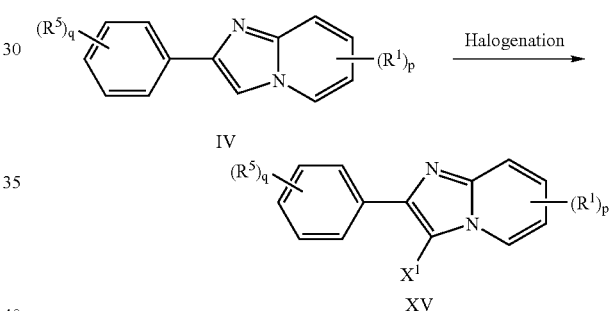

wherein all variables are as defined above in connection with Scheme 4.

Typically, the halogenation reaction is carried out by treating a compound of formula (IV) with a halogenating agent in a suitable solvent. Suitable halogenating agents include but are not limited to, iodine, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (IV) can be prepared according to the methods described above in connection with Scheme 1.

In addition to the foregoing process for preparing certain compounds of formula (I), the present invention also provides certain intermediate compounds for use in the preparation of such compounds of formula (I). Such intermediates are described in connection with Scheme 4 above.

Each of the foregoing processes may further comprise the step of converting the compound of formula (I) to a pharmaceutically acceptable salt, solvate, or physiologically functional derivative thereof, using techniques well known to those skilled in the art.

As will be apparent to those skilled in the art, a compound of formula (I) may be converted to another compound of formula (I) using techniques well known in the art. For example, a compound of formula (I-A), where one $R^1$ (i.e. denoted Hal) is halogen) may be converted to a compound of formula (I-B) using amination techniques known to those skilled in the art.

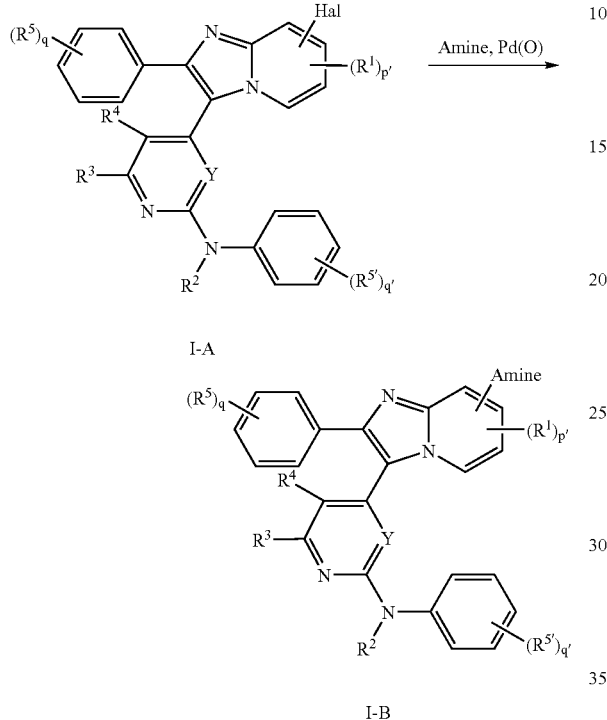

I-A

I-B wherein Hal is halo, particularly chloro, bromo or iodo; p' is p-1; Amine is a group selected from the group consisting of —$NR^7R^8$, —$NR^7Ay$, -Het bonded through N, and —NHHet, and all other variables are as defined in connection with any process above.

The reaction can be carried out via an adaptation of procedures found in the literature (Wolfe, J. P.; Buchwald, S. L. *J. Org. Chem.* 2000, 65, 1144) wherein a compound of the formula (I-A) is treated with a suitable amine group, a palladium (O) or nickel (O) source and a base, optionally in a suitable solvent, at temperature ranging from ambient temperature to 200° C. Suitable sources of palladium (O) include but are not limited to palladium(II) acetate and tris(dibenzylideneacetone) dipalladium (O). Typical bases for use in the reaction include, for example sodium tert-butoxide and cesium carbonate. The reaction can be carried out in neat amine or in a suitable solvent Toluene is an example of a suitable solvent.

As a further example, a compound of formula (I-C) (i.e., a compound of formula (I) wherein q is 1 or more and at least one $R^5$ is O-methyl) may be converted to a compound of formula (I-D) (i.e., a compound of formula (I) wherein q is 1 or more and at least one $R^5$ is OH) using conventional demethylation techniques. Additionally, a compound of formula (I-D) may optionally be converted to a compound of formula (I-E) (i.e., a compound of formula (I) wherein q is 1 or more and at least one $R^5$ is $OR^{10}$). For example, the foregoing conversions are represented schematically as follows:

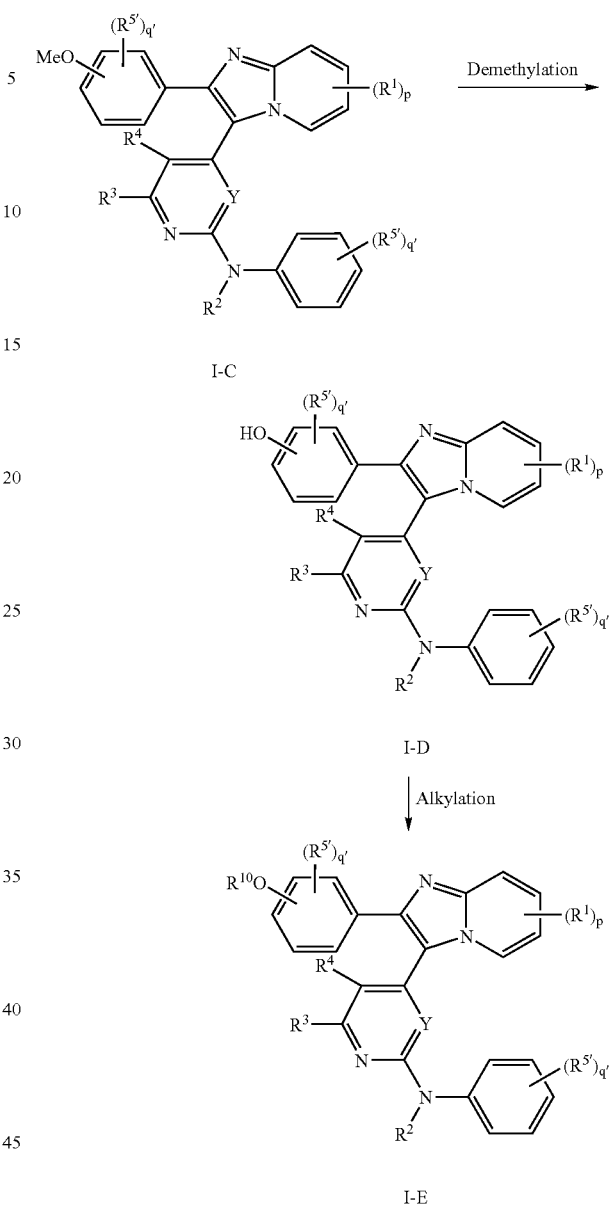

I-C

I-D

I-E wherein q" is q-1; Me is methyl and all other variables are as defined in connection with any process above.

The demethylation reaction may be carried out by treating a compound of formula (I-C) in a suitable solvent with a Lewis acid at a temperature of −78° C. to room temperature, to produce a compound of formula (I-D). Typically the solvent is an inert solvent such as dichloromethane, chloroform, acetonitrile, toluene or the like. The Lewis acid may be boron tribromide, trimethylsilyl iodide or the like.

Optionally, a compound of formula (I-D) may be further converted to a compound of formula (I-E) by an alkylation reaction. The alkylation reaction may be carried out by treating a compound of formula (I-D) in suitable solvent with an alkyl halide of formula $R^{10}$-Halo where $R^{10}$ is as defined above, to form another compound of formula (I-E). The reaction is typically carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

In yet another example, a compound of formula (I-F) (i.e., a compound of formula (I) wherein q is 1 or more and at least one $R^5$ is halo) or a compound of formula (I-H) (i.e. a compound of formula (I) wherein q is 1 or more and at least one $R_5$ is nitro) can be converted to a compound of formula (I-G) (i.e., a compound of formula (I) wherein q is 1 or more and at least one $R^5$ is $NH_2$). Optionally, a compound of formula (I-G) may then be converted to a compound of formula (I-I) (i.e., a compound of formula (I) wherein q is 1 or more and at least one $R^5$ is —$NR^7R^8$ where $R^7$ and $R^8$ are not both H). For example, the foregoing conversions are represented schematically as follows:

followed by hydrolysis to give a compound of formula (I-G). See J. Wolfe, et al., *Tetrahedron Letters* 38:6367–6370 (1997). Typically the imine is benzophenoneimine, the palladium (O) source is tris(dibenzylideneacetone)dipalladium (O), the base is sodium tert-butoxide and the ligand is racemic-2,2'-bis(diphenylphosphino)-1,1'-binaphthyl. Suitable solvents include N,N-dimethylformamide and the like.

A compound of formula (I-G) can also be obtained from a compound of formula (I-H) by reduction. The reduction can conveniently be carried out by using zinc, tin or iron and acid, by using tin(II)chloride, or by using palladium or platinum catalysts under hydrogen atmosphere in a suitable solvent as obvious to one skilled in the art of organic synthesis.

Reaction of a compound of formula (I-G) with compound of formula $R^7$-halogen in a suitable solvent in the presence of base, optionally with heating may be used to prepare a

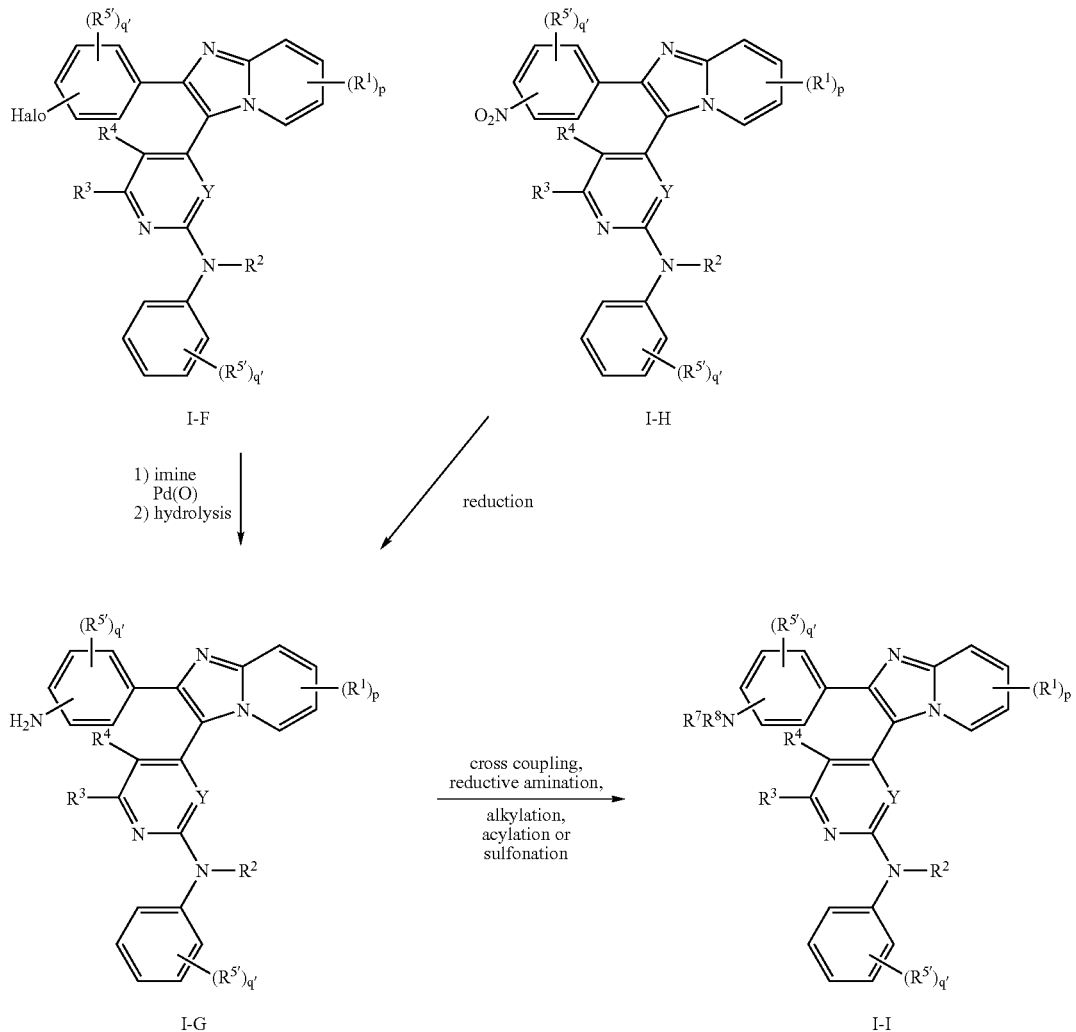

wherein q" is q-1 and all other variables are as defined in connection with any process above.

The process of converting a compound of formula (I-F) to a compound of formula (I-G) is carried out by reacting a compound of formula (I-F) with an imine in the presence of a palladium (O) source, a base and a suitable ligand, compound of formula (I-I). Typically the base is triethylamine or pyridine and the solvent is N,N-dimethylformamide and the like.

Additional a compound of formula (I-I) can be obtained by reductive amination of a compound of formula (I-G) with ketones or aldehydes. See, A. Abdel-Magid, et al., *J. Org.*

Chem. 61:3849–3862 (1996). Typically a compound of formula (I-G) is treated with an aldehyde or a ketone in the presence of an acid, such as acetic acid, and a reducing agent, such as sodium triacetoxyborohydride or the like, in an inert solvent such as dichloroethane or the like.

Other transformations well known to those skilled in the art for use with anilines may be used to convert a compound of formula (I-G) to a compound of formula (I-I). It will also be apparent to one skilled in the art that the transformations described above for the transformation of a compound of formula (I) to another compound of formula (I) whereby the substituents $R^1$ and/or $R^5$ are altered will be equally applicable to the substitutions denoted in formula (I) by $R^{5'}$.

As will be apparent to those skilled in the art, the steps of each of the foregoing syntheses can be rearranged according to conventional knowledge in the art. Hence, the order of the steps in the foreoing syntheses is not criticial to the practice of the present invention. All modifications to the synthesis exemplified here which would be obvious to those skilled in the art, are contemplated by the present invention.

Based upon this disclosure and the following examples contained herein one skilled in the art can readily convert a compound of formula (I) or a pharmaceutically acceptable salt, solvate or physiologically functional derivative thereof into another compound of formula (I) or a pharmaceutically acceptable salt, solvate or physiologically functional derivative thereof.

The present invention also provides a radiolabeled compound of formula (I) and a biotinylated compound of formula (I). Radiolabeled compounds of formula (I) and biotinylated compounds of formula (I) can be prepared using conventional techniques. For example, a radiolabeled compound of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and the biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compound of formula (I) to the target protein. More specifically, suitable assay methods will include competition binding assays. The radiolabeled compounds of formula (I) can be employed in assays according to the methods conventional in the art.

The following examples are illustrative embodiments of the invention, not limiting the scope of the invention in any way, the invention being defined by the claims which follow. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

4-[8-Chloro-2-(3-methoxyphenyl)imidazo[1,2-α] pyridin-3-yl]-N-phenylpyrimidin-2-amine

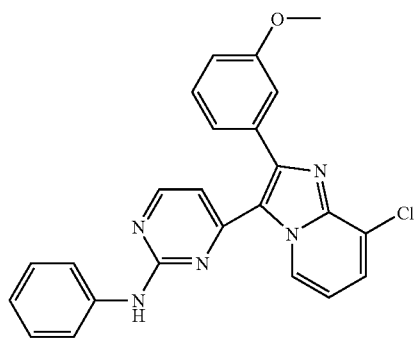

a) 2-Amino-3-chloropyridine 2,3-Dichloropyridine (20 g, 0.14 moles) was placed in a steel bomb. To this was added concentrated ammonium hydroxide (300 mL), the bomb sealed and heated at 190° C. for 48 hours. The vessel was cooled to room temperature and opened. Ethyl acetate and water were added. The phases were separated and the ethyl acetate phase washed with water, dried (magnesium sulfate), filtered and concentrated to a solid. This solid was crystallized from a small volume of ethyl acetate to give 12.6 g (70%) of 2-amino-3-chloropyridine as a white solid. $^1$H NMR (CDCl$_3$) δ 7.95 (dd, 1H), 7.46 (dd, 1H), 6.58 (q, 1H), 5.0 (broad s, 2H); MS m/z 129 (M+H).

b) 8-Chloro-2-(3-methoxyphenyl)imidazo[1,2-α] pyridine

To a solution of 3-chloro-2-pyridinamine (4.8 g, 37.4 mmol) and 2-bromo-1-(3-methoxyphenyl)ethanone (8.56 g, 37.4 mmol) in ethanol (30 mL) was added potassium carbonate (5.15 g, 37.4 mmol) and the resultant solution was heated at reflux for 17 hours. The reaction mixture was cooled to room temperature and concentrated in vacuo. The resultant residue was taken up in dichloromethane, washed with water and then brine. The aqueous layer was extracted with dichloromethane and the combined organics dried over magnesium sulfate. Filtration and concentration followed by recrystallization of the residue from ethyl acetate-hexanes reulted in 8-chloro-2-(3-methoxyphenyl)imidazo[1,2-α]pyridine (6.7 g, 70%) as a tan powder. $^1$H NMR (CDCl$_3$): δ 8.03 (d, 1 H), 7.89 (s, 1 H), 7.57–7.52 (m, 2 H), 7.33 (t, 1 H), 7.23 (d, 1 H), 6.89 (dd, 1 H), 6.71 (t, 1 H), 3.89 (s, 3 H); $^{13}$C NMR (CDCl$_3$): δ 159.94, 146.31, 142.96, 134.61, 129.65, 124.30, 123.58, 123.26, 118.81, 114.33, 112.02, 111.44, 109.91, 55.39; MS m/z 259 (M+1); Anal. Calcd for C$_{14}$H$_{11}$ClN$_2$O: C, 64.93; H, 4.29; N, 10.83. Found: C, 64.58; H, 4.51; N, 10.52.

c) 8-Chloro-2-(3-methoxyphenyl)imidazo[1,2-α]pyridine-3-carbaldehyde

N,N-Dimethylformamide (30 mL) was cooled to 0° C. and treated with phosphorous oxychloride (1.08 mL, 11.6 mmol). After the addition was complete, the mixture was warmed to room temperature and stirred for 10 minutes. To this was added 8-chloro-2-(3-methoxyphenyl)imidazo[1,2-α]pyridine (2.0 g, 7.75 mmol) and the resulting solution was stirred for 48 hours. Water was added to the reaction. The solids were then filtered and azeoptroped with methanol to give 8-chloro-2-(3-methoxyphenyl)imidazo[1,2-α]pyridine-3-carbaldehyde (2.2 g, 99%) as a white solid.

$^1$H NMR (CDCl$_3$): δ 10.09 (s, 1 H), 9.60 (d, 1 H), 7.64 (d, 1 H), 7.45–7.37 (m, 3 H), 7.09–7.05 (m, 2 H), 3.90 (s, 3 H); MS m/z 287 (M+1); Anal. Calcd. for C$_{15}$H$_{11}$ClN$_2$O$_2$: C, 62.84; H, 3.87; N, 9.77. Found: C, 62.79; H, 3.92; N, 9.64.

d) 1-[8-Chloro-2-(3-methoxyphenyl)imidazo[1,2-α]pyridin-3-yl]-2-propyn-1-ol

To a cold (−78° C.) solution of 8-chloro-2-(3-methoxyphenyl)imidazo[1,2-α]pyridine-3-carbaldehyde (1.06 g, 3.70 mmol) in tetrahydrofuran (20 mL) was added ethynyl magnesium bromide (18.53 mL, 0.5 M in tetrahydrofuran, 9.26 mmol). After 15 minutes, the resulting mixture was allowed to warm to room temperature and stirred an additional 30 minutes. Water was added and then ether. The organic layer was washed with brine. The aqueous layer was extracted with ether and the combined organics were dried over magnesium sulfate. Filtration and concentration followed by flash chromatography (1:1 hexanes-ethyl acetate to 100% ethyl acetate) provided 1-[8-chloro-2-(3-methoxyphenyl)imidazo[1,2-α]pyridin-3-yl]-2-propyn-1-ol (910 mg, 79%) as a white solid. $^1$H NMR (CDCl$_3$): δ 8.61 (d, 1 H), 7.33–7.26 (m, 2 H), 7.16–7.11 (m, 2 H), 6.88 (m, 1 H), 6.79 (m, 1 H), 6.14 (m, 1 H), 3.85 (s, 3 H), 3.27 (broad, 1 H), 2.64 (d, 1 H); $^{13}$C NMR (CDCl$_3$): δ 159.64, 144.46, 134.12, 129.56, 124.99, 124.51, 123.03, 121.37, 119.43, 114.54, 114.13, 111.81, 111.27, 79.96, 75.03, 55.88, 55.38; MS m/z 313 (M+1); Anal. Calcd. for C$_{17}$H$_{13}$ClN$_2$O$_2$: C, 65.29; H, 4.19; N, 8.96. Found: C, 65.23; H, 4.34; N, 8.81.

e) 1-[8-Chloro-2-(3-methoxyphenyl)imidazo[1,2-α]pyridin-3-yl]-2-propyn-1-one To a solution of 1-[8-chloro-2-(3-methoxyphenyl)imidazo[1,2-α]pyridin-3-yl]-2-propyn-1-ol (870 mg, 2.78 mmol) in dichloromethane (150 mL) was added manganese dioxide (9.6 g, 111 mmol) and the resulting suspension was stirred at room temperature for 1.5 hours. The mixture was filtered through Celite. The filtrate was concentrated in vacuo to give 1-[8-chloro-2-(3-methoxyphenyl)imidazo[1,2-α]pyridin-3-yl]-2-propyn-1-one (680 mg, 78%) as a golden foam. $^1$H NMR (CDCl$_3$): δ 9.66 (d, 1 H), 7.65 (d, 1 H), 7.34 (t, 1 H), 7.28–7.22 (m, 2 H), 7.10 (t, 1 H), 7.02 (m, 1 H), 3.86 (s, 3 H), 2.86 (s, 1 H); MS m/z 311 (M+1).

f) N-Phenylguanidinium Nitrate

To a room temperature solution of aniline (10.0 g, 107 mmol) in ethanol (100 mL) was added cyanamide (9.6 mL, 50 wt % in water, 123 mmol) followed by the dropwise addition of concentrated nitric acid (7.56 mL). The mixture was heated at reflux for 3.5 hours and allowed to cool to room temperature. The mixture was concentrated in vacuo and the residue was crystallized from methanol/ethyl acetate/dichloromethane to yield N-phenylguanidinium nitrate (6.7 g, 32%) as a white crystalline solid. $^1$H NMR (DMSO-d$_6$): δ 9.63 (s, 1 H), 7.44 (t, 2 H), 7.37 (broad s, 3 H), 7.29 (t, 1 H), 7.23 (d, 2 H);
$^{13}$C NMR (DMSO-d$_6$): δ 156.36, 135.99, 130.40, 127.19, 125.18; MS m/z 136 (M+1 of free base).

g) 4-[8-Chloro-2-(3-methoxyphenyl)imidazo[1,2-α]pyridin-3-yl]-N-phenylpyrimidin-2-amine To a solution of 1-[8-chloro-2-(3-methoxyphenyl)imidazo[1,2-α]pyridin-3-yl]-2-propyn-1-one (58 mg, 0.19 mmol) in 1-methyl-2-pyrrolidinone (2 mL) was added N-phenylguanidinium nitrate (185 mg, 0.94 mmol) and potassium carbonate (129 mg, 0.94 mmol). The mixture was heated at 140° C. for 1.25 hours and then cooled to room temperature. Water was added then ether. The organic layer was washed with brine. The aqueous layer was extracted with ether and the combined organics dried over magnesium sulfate. Filtration and concentration followed by flash chromatography (2:1 hexanes-ethyl acetate) provided 4-[8-chloro-2-(3-methoxyphenyl)imidazo[1,2-α]pyridin-3-yl]-N-phenylpyrimidin-2-amine (40 mg, 50%) as a yellow solid. $^1$H NMR (CDCl$_3$ with 2 drops CD$_3$OD): δ 9.45 (d, 1 H), 8.16 (d, 1 H), 7.60–7.58 (m, 2 H), 7.39 (d, 1 H), 7.34–7.29 (m, 3 H), 7.17–7.15 (m, 2 H), 7.07 (t, 1 H), 6.95 (m, 1 H), 6.75 (t, 1 H), 6.58 (d, 1 H), 3.79 (s, 3 H); MS m/z 428 (M+1).

EXAMPLE 2

N-Cyclopentyl-3-[2-(cyclopentylamino)-4-pyrimidinyl]-2-(3-methoxyphenyl)imidazo[1,2-α]pyridin-8-amine

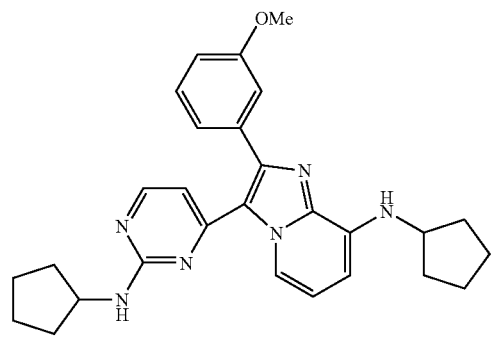

To a solution of 4-[8-chloro-2-(3-methoxyphenyl)imidazo[1,2-α]pyridin-3-yl]-N-phenylpyrimidin-2-amine (162 mg, 0.39 mmol) in cyclopentylamine (5 mL) was added, successively, racemic-2,2'-bis(diphenylphosphino)-1,1'-binaphthyl (15.3 mg, 0.02 mmol), cesium carbonate (376 mg, 1.15 mmol) and palladium (II) acetate (3.5 mg, 0.015 mmol). The resulting mixture was heated in a sealed tube at 150° C. for 24 hours at which time the reaction was judged complete by thin layer chromatography. The solution was cooled to room temperature and ethyl acetate and water were added. The phases were separated and the organic layer was washed with water and brine. The combined organics were dried over magnesium sulfate, filtered and concentrated. The residue was purified by flash chromatography (2:1 hexanes-ethyl acetate) to give N-cyclopentyl-3-[2-(cyclopentylamino)-4-pyrimidinyl]-2-(3-methoxyphenyl)imidazo[1,2-α]pyridin-8-amine (55 mg, 31%) as a white solid. $^1$H NMR (CDCl$_3$): δ 8.90 (m, 1 H), 8.08 (d, 1 H), 7.37–7.22 (m, 2 H), 6.96 (m, 1 H), 6.79 (t, 1 H), 6.43 (d, 1 H), 6.30 (d, 1 H), 5.40 (d, 1 H), 5.31 (d, 1 H), 4.37 (m, 1 H), 3.94 (m, 1 H), 3.85 (s, 3 H), 2.14–2.07 (m, 4 H), 1.82–1.56 (m, 12 H); MS m/z 469 (M+1).

EXAMPLE 3

4-[8-Chloro-2-(4-methylphenyl)imidazo[1,2-α]pyridin-3-yl]-N-phenylpyrimidin-2-amine

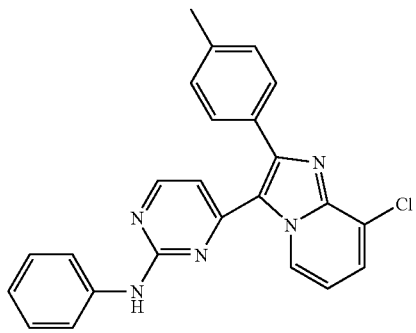

a) 8-Chloro-2-(4-methylphenyl)imidazo[1,2-α]pyridine

In a similar manner as described in Example 1 from 2-bromo-1-(4-methylphenyl)ethanone (3.5 g, 16.4 mmol) and 3-chloro-2-pyridinamine (2.1 g, 16.4 mmol) was formed 8-chloro-2-(4-methylphenyl)imidazo[1,2-α]pyridine (4 g, 99%) as a white solid. $^1$H NMR (CDCl$_3$): δ 8.06 (d, 1 H), 7.90 (d, 2 H), 7.89 (s, 1 H), 7.26 (d, 2 H), 7.24 (d, 1 H), 6.72 (t, 1 H), 2.40 (s, 3 H); MS m/z 243 (M+1).

b) 8-Chloro-2-(4-methyl phenyl)imidazo[1,2-α]pyridine-3-carbaldehyde

In a similar manner as described in Example 1 from 8-chloro-2-(4-methylphenyl)imidazo[1,2-α]pyridine (4 g, 16.4 mmol) and phosphorous oxychloride (2.29 mL, 24.6 mmol) in N,N-dimethylformamide (50 mL) was formed 8-chloro-2-(4-methylphenyl)imidazo[1,2-α]pyridine-3-carbaldehyde (1.7 g, 38%) as a white solid. $^1$H NMR (CDCl$_3$): δ 10.09 (s, 1 H), 9.61 (d, 1 H), 7.77 (d, 2 H), 7.64 (d, 1 H), 7.35 (d, 2 H), 7.06 (t, 1 H), 2.46 (s, 3 H); $^{13}$C NMR (CDCl$_3$): δ 180.07, 158.51, 145.16, 140.34, 129.93, 129.62, 129.15, 129.01, 127.26, 123.40, 121.69, 114.81, 21.42; MS m/z 271 (M+1).

c) 1-[8-Chloro-2-(4-methylphenyl)imidazo[1,2-α]pyridin-3-yl]-2-propyn-1-ol

In a similar manner as described in Example 1 from 8-chloro-2-(4 methylphenyl)imidazo[1,2-α]pyridine-3-carbaldehyde (1.04 g, 3.85 mmol) and ethynyl magnesium bromide (19.25 mL, 0.5 M in tetrahydrofuran, 9.62 mmol) was formed 1-[8-chloro-2-(4-methylphenyl)imidazo[1,2-α]pyridin-3-yl]-2-propyn-1-ol (1.1 g, 99%) as a white solid. $^1$H NMR (CDCl$_3$): δ 8.57 (d, 1 H), 7.37 (d, 2 H), 7.26 (m, 1 H), 7.10 (d, 2 H), 6.75 (t, 1 H), 6.10 (d, 1 H), 3.71 (broad, 1 H), 2.62 (d, 1 H), 2.33 (s, 3 H); MS m/z 297 (M+1).

d) 1-[8-Chloro-2-(4-methylphenyl)imidazo[1,2-α]pyridin-3-yl]-2-propyn-1-one

In a similar manner as described in Example 1 from 1-[8-chloro-2-(4-methylphenyl)imidazo[1,2-α]pyridin-3-yl]-2-propyn-1-ol (1.10 g, 3.71 mmol) was formed 1-[8-chloro-2-(4-methylphenyl)imidazo[1,2-α]pyridin-3-yl]-2-propyn-1-one (943 mg, 870%) as a brown solid. $^1$H NMR (CDCl$_3$): δ 9.68 (d, 1 H), 7.67–7.61 (m, 3 H), 7.27–7.07 (m, 3 H), 2.86 (s, 1 H), 2.44 (s, 3 H); MS m/z 295 (M+1).

e) 4-[8-Chloro-2-(4-methylphenyl)imidazo[1,2-α]pyridin-3-yl]-N-phenylpyrimidin-2-amine In a similar manner as described in Example 1 from 1-[8-chloro-2-(4-methylphenyl)imidazo[1,2-α]pyridin-3-yl]-2-propyn-1-one (200 mg, 0.68 mmol) and N-phenylguanidine nitrate (673 mg, 3.40 mmol) was formed 4-[8-chloro-2-(4-methylphenyl)imidazo[1,2-α]pyridin-3-yl]-N-phenyl-2-pyrimidinamine (117 mg, 42%) as a white solid. $^1$H NMR (CDCl$_3$): δ 9.46 (d, 1 H), 8.22 (d, 1 H), 7.63 (d, 2 H), 7.56 (d, 2H), 7.41–7.34 (m, 3 H), 7.25–7.22 (m, 3 H), 7.10 (t, 1 H), 6.77 (t, 1 H), 6.66 (d, 1 H), 2.41 (s, 3 H); MS m/z 412 (M+1).

EXAMPLE 4

3-(2-Anilino-4-pyrimidinyl)-N-cyclopentyl-2-(4-methylphenyl)imidazo[1,2-α]pyridin-8-amine

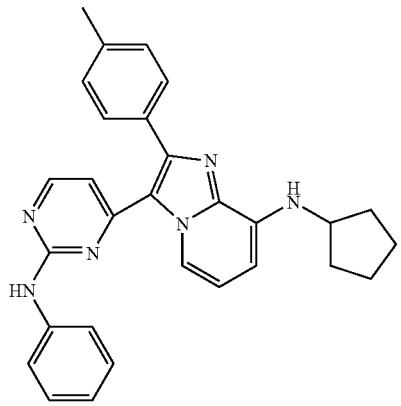

In a similar manner as described in Example 2 from 4-[8-chloro-2-(4-methylphenyl)imidazo[1,2-α]pyridin-3-yl]-N-phenyl-2-pyrimidinamine (95 mg, 0.23 mmol) and cyclopentylamine was formed 3-(2-anilino-4-pyrimidinyl)-N-cyclopentyl-2-(4-methylphenyl)imidazo[1,2-α]pyridin-8-amine (17 mg, 16%) as a yellow solid. $^1$H NMR (CDCl$_3$): δ 8.80 (d, 1 H), 8.16 (d, 1 H), 7.64 (d, 2 H), 7.52 (m, 2 H), 7.40 (s, 1 H), 7.34 (m, 2 H), 7.22 (m, 2 H), 7.06 (t, 1 H), 6.70 (t, 1 H), 6.59 (d, 1 H), 6.26 (d, 1 H), 5.28 (m, 1 H), 3.91 (m, 1 H), 2.40 (s, 3 H), 2.10–2.04 (m, 2 H), 1.82–1.62 (m, 6H); MS m/z 461 (M+1).

EXAMPLE 5

4-[8-Chloro-2-(3-nitrophenyl)imidazo[1,2-α]pyridin-3-yl]-N-(4-fluorophenyl)pyrimidin-2-amine

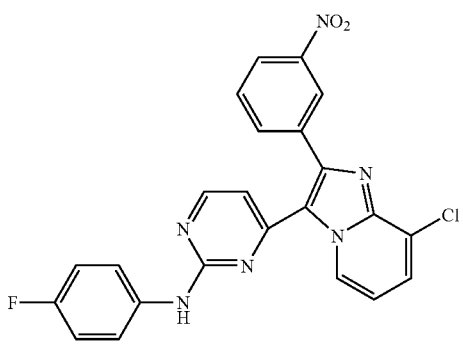

a) 8-Chloro-2-(3-nitrophenyl)imidazo[1,2-α]pyridine

In a similar manner as described in Example 1 from 2-bromo-1-(3-nitrophenyl)ethanone (4.27 g, 17.5 mmol) and 3-chloro-2-pyridinamine (2.25 g, 17.5 mmol) was formed 8-chloro-2-(3-nitrophenyl)imidazo[1,2-α]pyridine (2.80 g, 59%) as a white solid. $^1$H NMR (CDCl$_3$): δ 8.76 (m, 1 H), 8.40 (d, $_1$H), 8.18 (m, 1 H), 8.11 (d, 1H), 8.04 (s, 1 H), 7.62 (t, 1 H), 7.30 (d, 1 H), 6.79 (t, 1 H); $^{13}$C NMR (CDCl$_3$): δ 148.65, 144.03, 143.35, 135.11, 132.26, 129.72, 124.51, 124.33, 123.66, 122.82, 120.97, 112.64, 110.56; MS m/z 274 (M+1); Anal. Calcd. for $C_{13}H_8ClN_3O_2$: C, 57.05; H, 2.95; N, 15.35. Found: C, 57.13; H, 3.01; N, 15.20.

b) 8-Chloro-2-(3-nitrophenyl)imidazo[1,2-α]pyridine-3-carbaldehyde

In a similar manner as described in Example 1 from 8-chloro-2-(3-nitrophenyl)imidazo[1,2-α]pyridine (2.40 g, 8.79 mmol) and phosphorous oxychloride (1.23 mL, 13.18 mmol) in N,N-dimethylformamide (25 mL) was formed 8-chloro-2-(3-nitrophenyl)imidazo[1,2-α]pyridine-3-carbaldehyde (1.7 g, 38%) as a white solid. $^1$H NMR (DMSO-d$_6$): δ 10.11 (s, 1 H), 9.54 (d, 1 H), 8.72 (s, 1 H), 8.43–8.40 (m, 2 H), 7.98 (d, 1 H), 7.87 (t, 1 H), 7.36 (t, 1 H); MS m/z 302 (M+1).

c) 1-[8-Chloro-2-(3-nitrophenyl)imidazo[1,2-α]pyridin-3-yl]-2-propyn-1-ol

In a similar manner as described in Example 1 from 8-chloro-2-(3-nitrophenyl)imidazo[1,2-α]pyridine-3-carbaldehyde (2.70 g, 8.97 mmol) and ethynyl magnesium bromide (54 mL, 0.5 M in tetrahydrofuran, 26.9 mmol) was formed 1-[8-chloro-2-(3-nitrophenyl)imidazo[1,2-α]pyridin-3-yl]-2-propyn-1-ol (2.60 g, 89%) as a white solid. $^1$H NMR (DMSO-d$_6$): δ 8.73 (d, 1 H), 8.57 (m, 1 H), 8.29 (dd, 1 H), 8.19 (d, 1 H), 7.83 (t, 1 H), 7.64 (t, 1 H), 7.11 (t, 1 H), 6.64 (d, 1 H), 6.09 (m, 1 H), 3.67 (d, 1 H); MS m/z 328 (M+1).

d) 1-[8-Chloro-2-(3-nitrophenyl)imidazo[1,2-α]pyridin-3-yl]-2-propyn-1-one

In a similar manner as described in Example 1 from 1-[8-chloro-2-(3-nitrophenyl)imidazo[1,2-α]pyridin-3-yl]-2-propyn-1-ol (2.5 g, 7.64 mmol) was formed 1-[8-chloro-2-(3-nitrophenyl)imidazo[1,2-α]pyridin-3-yl]-2-propyn-1-one (2.20 g, 88%) as a brown solid. $^1$H NMR (DMSO-d$_6$): δ 9.54 (d, 1 H), 8.57 (s, 1 H), 8.39 (d, 1 H), 8.18 (d, 1 H), 7.98 (d, 1 H), 7.77 (t, 1 H), 7.37 (t, 1 H), 4.46 (s, 1 H); MS m/z 326 (M+1).

e) N-(4-Fluorophenyl)guanidine nitrate

In a similar manner as described in Example 1 from 4-fluoroaniline (10 g, 90 mmol) was obtained N-(4-fluorophenyl)guanidine nitrate (7.13 g, 37%) as a powder. $^1$H NMR (D$_2$O): δ 7.23–7.08 (m, 4H); $^{19}$F NMR (D$_2$O) δ −114.38; $^{13}$C NMR (D$_2$O) δ 161.99 (d, $J_{CF}$=243.5 Hz), 156.83, 130.18 (d, $J_{CF}$=3.0 Hz), 128.76 (d, $J_{CF}$=9.1 Hz), 116.87 (d, $J_{CF}$=22.8 Hz); MS m/z 154 (M+1 of free base).

f) 4-[8-Chloro-2-(3-nitrophenyl)imidazo[1,2-α]pyridin-3-yl]-N-(4-fluorophenyl)-2-pyrimidinamine In a similar manner as described in Example 1 from 1-[8-chloro-2-(3-nitrophenyl)imidazo[1,2-α]pyridin-3-yl]-2-propyn-1-one (220 mg, 0.68 mmol) and N-(4-fluorophenyl)guanidine nitrate (728 mg, 3.38 mmol) was formed 4-[8-chloro-2-(3-nitrophenyl)imidazo[1,2-α]pyridin-3-yl]-N-(4-fluorophenyl)-2-pyrimidinamine (40 mg, 13%) as a white solid. $^1$H NMR (DMSO-d$_6$): δ 9.92 (s, 1 H), 9.29 (d, 1 H), 8.54–8.48 (m, 2 H), 8.32 (m, 1 H), 8.14 (m, 1 H), 7.80–7.72 (m, 4 H), 7.17–7.11 (m, 3 H), 6.80 (d, 1 H); $^{19}$F NMR (DMSO-d$_6$): δ −121.63; MS m/z 461 (M+1).

EXAMPLE 6

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV infection.

Vero 76 cells were maintained in MEM with Earle's salts, L-glutamine, 8% FBS (Hyclone, A-1111-L) and 100 units/mL Penicillin-100 µg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 µL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 µM primers, 180 µM dTTP, 20 µM dUTP-digoxigenin (Boehringer Mannheim 1558706), 200 µM each of dATP, dCTP, and dGTP, 1×PCR Buffer II (Perkin Elmer), 2.5 mM $MgCl_2$, 0.025 units/µL of AmpliTaq Gold polymerase (Perkin Elmer), and 5 ng of gel-purified HSV DNA per 100 µL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 µg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/µL 75 µL/well were added to Corning (#3922 or 9690) white 96-well plates and incubated at room temperature for at least 4 hrs before washing twice with 300 µL/well 0.2×SSC/0.05% Tween-20 (SSC/T buffer). The plates were then incubated overnight at room temperature with 150 µL/well 0.2 N NaOH, 1% IGEPAL and 10 µg/mL herring sperm DNA.

(d) Hybridization.

Twenty-seven (27) µL of cell lysate was combined with 45 mL of hybridization solution (final concentration: 3M GuSCN, 50 mM EDTA, 100 µg/ml salmon sperm DNA, 5× Denhardt's solution, 0.25×APE, and 5 ng of the digoxigenin-labeled detection probe). APE is 1.5 M $NH_4$-acetate, 0.15 M ammonium phosphate monobasic, and 5 mM EDTA adjusted to pH 6.0. Mineral oil (50 µL) was added to prevent evaporation. The hybridization plates were incubated at 95° C. for 10 minutes to denature the DNA, then incubated at 42° C. overnight. The wells were washed 6× with 300 µL/well SSC/T buffer then incubated with 75 mL/well anti-digoxigenin-HRP-conjugated antibody (Boehringer Mannheim 1207733, 1:5000 in TE) for 30 min at room temperature. The wells were washed 6× with 300 µL/well with PBS/0.05% Tween-20 before 75 µL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | $IC_{50}$ (µM) |
|---|---|
| 1 | 1.46 |
| 2 | 0.35 |
| 3 | 3.52 |
| 4 | 3.54 |
| 5 | 2.23 |

The results demonstrate that the compounds of the present invention are useful for the treatment and prophylaxis of herpes viral infections.

The invention claimed is:

1. A compound of formula (I):

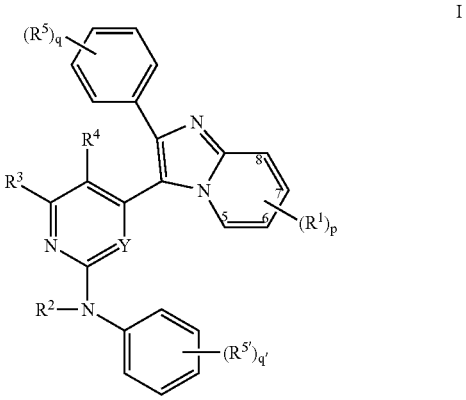

wherein:
  p is 0, 1 or 2;
  each $R^1$ is the same or different and is independently selected from the group consisting of halo, alkyl, Het, $OR^7$, —C(O)Het, —S(O)$_n R^9$, —S(O)$_2 NR^7 R^8$, —$NR^7 R^8$, —$NR^7 Ay$, —NHHet,
  wherein when p is 1, $R^1$ is in the C-8 position or C-6 position, and when p is 2, one $R^1$ is in the C-8 position and one $R^1$ is in the C-6 position;
  each $R^7$ and $R^8$ are the same or different and are independently selected from the group consisting of H, alkyl, alkenyl, cycloalkyl, cycloalkenyl, —C(O) $R^9$, —$CO_2 R^9$, —C(O)$NR^9 R^{11}$—C(NH)$NR^9 R^{11}$, —$SO_2 R^{10}$, —$SO_2 NR^9 R^{11}$, —$R^{10}$cycloalkyl, —$R^{10}OR^9$ and —$R^{10}NR^9 R^{11}$;
  each $R^9$ and $R^{11}$ are the same or different and are independently selected from the group consisting of H, alkyl, cycloalkyl, —$R^{10}$cycloalkyl, —$R^{10}$OH, —$R^{10}(OR^{10})_w$ where w is 1–10, and —$R^{10}NR^{10}R^{10}$;
  each $R^{10}$ is the same or different and is independently selected from the group consisting of alkyl, cycloalkyl, alkenyl, cydoalkenyl and alkynyl;
  Ay is aryl;
  Het is a 5- or 6-membered heterocyclic or heteroaryl group;
  $R^2$ is selected from the group consisting of H, alkyl and cycloalkyl;
  n is 0, 1 or 2;
  Y is N;
  $R^3$ and $R^4$ are the same or different and are each independently selected from the group consisting of H, halo, alkyl, alkenyl, cycloalkyl, Ay, Het, —$OR^7$, —C(O)$R^7$, —$CO_2 R^7$, —$SO_2 NHR^9$, —$NR^7 R^8$, —NH-Het and —$NHR^{10}$Het;
  q and q' are the same or different and are each independently selected from the group consisting of 0, 1, 2 and 3; and
  each $R_5$ and $R^{5'}$ are the same or different and are independently selected from the group consisting of halo, alkyl, alkenyl, alkynyl, cycfoalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2 R^9$, —C(O) $NR^7 R^8$, —C(O)$NR^7 Ay$, —C(O)$NHR^{10}$Het, —C(S)

NR⁹R¹¹, —C(NH)NR⁷R⁸, —C(NH)NR⁷Ay, —S(O)ₙR⁹, —S(O)₂NR⁷R⁸, —S(O)NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰(O)R⁹, —R¹⁰CO₂R⁸, —R¹⁰(O)NR⁹R¹¹, —R¹⁰(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁵ or R⁵ groups together with the atoms to which they are bonded form a C₅₋₆ cycloalkyl or aryl;

or a pharmaceutically acceptable salt thereof.

2. The compound according to claim 1 wherein p is 1 or 2.

3. The compound according to claim 1 wherein R² is H or alkyl.

4. The compound according to claim 1 wherein R² is H.

5. The compound according to claim 1 wherein R³ and R⁴ are the same or different and are each independently selected from the group consisting of H, halo, alkyl, Ay, —OR⁷, —CO₂R⁷ and —NR⁷R⁸.

6. The compound according to claim 1 wherein R³ and R⁴ are each independently H or alkyl.

7. The compound according to claim 1 wherein q and q' are the same or different and are each independently selected from the group consisting of 0, 1 and 2.

8. The compound according to claim 1 wherein each R₅ is the same or different and is independently selected from the group consisting of halo, alkyl, Ay, Het, —OR⁷, —OAy, —CO₂R⁹, —C(O)NR⁷R⁸, —S(O)₂NR⁷R⁸, —NR⁷R⁸, —NR⁷Ay, —NHR¹⁰Ay, cyano, nitro and azido.

9. The compound according to claim 1, wherein each R⁵ is the same or different and is independently selected from the group consisting of halo, alkyl, —OR⁷, —NR⁷R⁸ and cyano.

10. The compound according to claim 1 wherein each R⁵' is the same or different and is independently selected from the group consisting of halo, alkyl, Ay, Het, —OR⁷, —OAy, —C(O)Ay, —C(O)Het, —CO₂R⁹, —C(O)NR⁷R⁸, —S(O)₂NR⁷R⁸, —NR⁷R⁸, cyano, nitro and azido.

11. The compound according to claim 1, wherein each R⁵' is the same or different and is independently selected from the group consisting of halo, alkyl, —OR⁷, —C(O)Ay, —C(O)Het and —NR⁷R⁸.

12. A compound selected from the group consisting of:
4[-Chloro-2-(3-methoxyphenyl)imidazo[1,2-a]pyridin-3-yl-]-N-phenylpyrimidin-2-amine:
4-[8-Chloro-2-(4-methylphenyl)imidazo[1,2-a]pyridin-3-yl]-N-phenylpyrimidin-2-amine;
3-(2-Anilino-4-pyrimidinyl)-N-cyclopentyl-2-(4-methylphenyl)imidazo[1,2-a]pyridin-8-amine; and
4-[8-Chloro-2-(3-nitrophenyl)imidazo[1,2-a]pyridin-3-yl]-N-(4-fluorophenyl)pyrimidin-2-amine;

or a pharmaceutically acceptable salt, thereof.

13. A pharmaceutical composition comprising a compound according to claim 1.

14. The pharmaceutical composition according to claim 13 further comprising a pharmaceutically acceptable carrier or diluent.

15. The pharmaceutical composition according to claim 11, further comprising an antiviral agent selected from the group consisting of aciclovir and valaciclovir.

16. A method for the treatment of a viral infection selected from herpes simplex virus 1 and herpes simplex virus 2 in an animal, said method comprising administering to the animal a therapeutically effective amount of a compound according to claim 1.

17. A method for the treatment of a condition or disease associated with a herpes viral infection selected from herpes simplex virus 1 and herpes simplex virus 2 in an animal, comprising administering to the animal a therapeutically effective amount of a compound according to claim 1.

18. A process for preparing the compound according to claim 1 wherein R₃ and R⁴ are H, said process comprising reacting a compound of formula (VI):

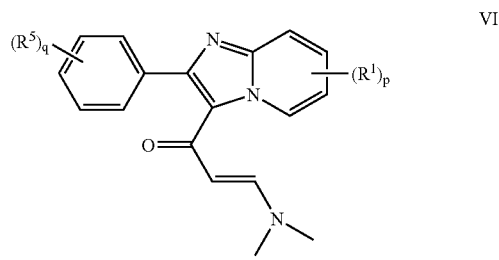

VI

With a compound of formula (VII):

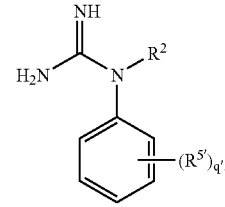

VII

19. A process for preparing the compound according to claim 1 wherein R³ is selected from the group consisting of H, alkyl, alkenyl, cycloalkyl, Ay, Het, —C(O)R⁷, —CO₂R⁷, —SO₂NHR⁹ and —NR⁷R⁸ (where R⁷ and R⁸ are not H); and R⁴ is H, said process comprising reacting a compound of formula (XI):

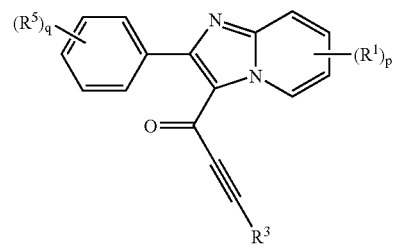

with a compound of formula (VII):

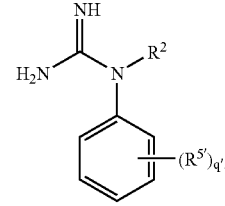

VII

20. A process for preparing the compound according to claim 1, said process comprising reacting a compound of formula (XIV):

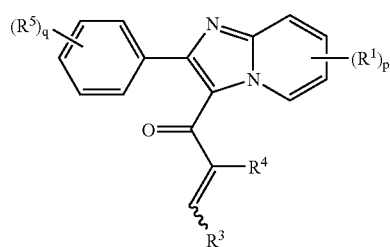

with a compound of formula (VII):

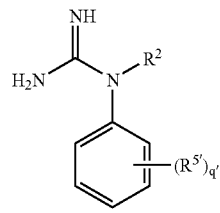

followed by oxidation to prepare the compound of formula (I).

21. A process for preparing the compound according to claim 1,
said process comprising reacting a compound of formula (VV):

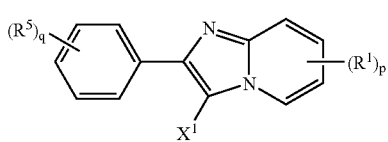

wherein $X^1$ is halo;
with a compound of formula (XVI):

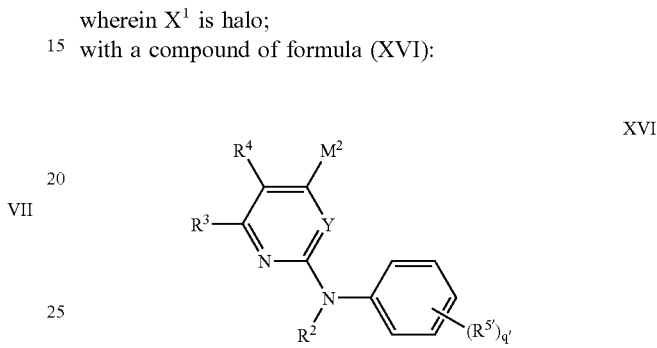

wherein $M^2$ is —B(OH)$_2$, —B(ORa)$_2$, —B(Ra)$_2$, —Sn(Ra)$_3$, Zn-halide, ZnRa or Mg-halide where Ra is alkyl or cycloalkyl and halide is halo.

* * * * *

UNITED STATES PATENT AND TRADEMARK OFFICE
CERTIFICATE OF CORRECTION

PATENT NO. : 7,244,740 B2
APPLICATION NO. : 10/489056
DATED : July 17, 2007
INVENTOR(S) : Gudmundsson et al.

It is certified that error appears in the above-identified patent and that said Letters Patent is hereby corrected as shown below:

Title Page;
Cover sheet (Foreign Patent Documents) reads:
"WO EP 0 364 204 A1 10/1989"
Should read:
-- EP 0 364 204 A1 10/1989 --

Cover sheet should read:
-- (74) Attorney, Agent, or Firm — Lorie A. Morgan --

Column 54, Claim 1, line 37 should read:
-- $R^9$, -$CO_2R^9$, -C(O)$NR^9R^{11}$, -C(NH)$NR^9R^{11}$, --

Column 54, Claim 1, line 46 should read:
-- cycloalkyl, alkenyl, cycloalkenyl and alkynyl; --

Column 54, Claim 1, line 62 should read:
-- each $R^5$ and $R^{5'}$ are the same or different and are inde --

Column 54, Claim 1, line 64 should read:
-- alkyl, alkenyl, alkynyl, cycloalkyl, cycloalkenyl, Ay, --

Column 55, Claim 1, line 2 should read:
-- $R^9$, -$S(O)_2NR^7R^8$, -$S(O)_2NR^7Ay$, -$NR^7R^8$, --

Column 55, Claim 1, line 4 should read:
-- $R^{10}$cycloalkyl, -$R^{10}$Het, –$R^{10}OR^9$, –$R^{10}C(O)R^9$, --

Column 55, Claim 1, line 5 should read:
-- -$R^{10}CO_2R^9$, -$R^{10}C(O)NR^9R^{11}$, -$R^{10}C(O)NR^7Ay$, --

Column 55, Claim 1, line 10 should read:
-- two adjacent $R^5$ or $R^{5'}$ groups together with the atoms to --

Column 55, Claim 5, line 21 should read:
-- -$CO_2R^7$ and –$NR^7R^8$ --

Column 55, Claim 12, line 46 should read:
-- 4[8-Chloro-2-(3-methoxyphenyl)imidazo[1,2-a]pyridine-3- --

UNITED STATES PATENT AND TRADEMARK OFFICE
CERTIFICATE OF CORRECTION

PATENT NO. : 7,244,740 B2
APPLICATION NO. : 10/489056
DATED : July 17, 2007
INVENTOR(S) : Gudmundsson et al.

It is certified that error appears in the above-identified patent and that said Letters Patent is hereby corrected as shown below:

Column 55, Claim 15, line 61 should read:
-- 13, further comprising an antiviral agent selected from the --

Column 56, Claim 18, line 7 should read:
-- claim 1 wherein $R^3$ and $R^4$ are H, said process comprising --

Column 58, Claim 21, line 4 should read:
-- (XV): --

Signed and Sealed this

Fifteenth Day of April, 2008

JON W. DUDAS
*Director of the United States Patent and Trademark Office*